(12) United States Patent
Pinchot

(10) Patent No.: US 6,994,245 B2
(45) Date of Patent: Feb. 7, 2006

(54) MICRO-REACTOR FABRICATION

(75) Inventor: James M. Pinchot, 2906 Commonwealth, Parma, OH (US) 44134

(73) Assignee: James M. Pinchot, Cleveland, OH (US)

(*) Notice: Subject to any disclaimer, the term of this patent is extended or adjusted under 35 U.S.C. 154(b) by 235 days.

(21) Appl. No.: 10/688,233

(22) Filed: Oct. 17, 2003

(65) Prior Publication Data
US 2005/0082351 A1 Apr. 21, 2005

(51) Int. Cl.
B23K 31/12 (2006.01)

(52) U.S. Cl. .................. 228/254; 228/103; 29/890; 422/191; 165/166; 700/98

(58) Field of Classification Search .......... 422/191; 228/103, 254
See application file for complete search history.

(56) References Cited

U.S. PATENT DOCUMENTS

| | | |
|---|---|---|
| 3,701,619 A | 10/1972 | Appeldoom |
| 3,881,701 A | 5/1975 | Schoenman et al. |
| 3,988,589 A | 10/1976 | Leask |
| 4,450,706 A | 5/1984 | Engelmohr |
| 4,516,632 A | 5/1985 | Swift et al. |
| 4,869,421 A | 9/1989 | Norris et al. |
| 4,951,305 A | 8/1990 | Moore et al. |
| 5,031,483 A | 7/1991 | Weaver |
| 5,071,503 A | 12/1991 | Berman |
| 5,137,369 A | 8/1992 | Hodan |
| 5,250,263 A | 10/1993 | Manz |
| 5,398,193 A | 3/1995 | deAngelis |
| 5,514,232 A | 5/1996 | Burns |
| 5,534,328 A | 7/1996 | Ashmead et al. |
| 5,544,771 A | 8/1996 | Lee et al. |
| 5,580,523 A | 12/1996 | Bard |
| 5,595,712 A | 1/1997 | Harbster et al. |
| 5,606,589 A | 2/1997 | Pellegrino |
| 5,658,537 A | 8/1997 | Dugan |
| 5,683,828 A | 11/1997 | Spear et al. |
| 5,690,763 A | 11/1997 | Ashmead et al. |
| 5,727,618 A | 3/1998 | Mundinger et al. |
| 5,779,833 A | 7/1998 | Cawley et al. |
| 5,843,385 A | 12/1998 | Dugan |
| 5,847,958 A | 12/1998 | Shaikh et al. |
| 5,872,714 A | 2/1999 | Shaikh et al. |
| 5,961,932 A | 10/1999 | Ghosh et al. |
| 5,993,750 A | 11/1999 | Ghosh et al. |
| 6,048,432 A | 4/2000 | Ecer |
| 6,129,973 A | 10/2000 | Martin et al. |
| 6,167,910 B1 | 1/2001 | Chow |
| 6,185,278 B1 | 2/2001 | Appleby et al. |
| 6,240,161 B1 | 5/2001 | Siochi |
| 6,271,524 B1 | 8/2001 | Wainer et al. |
| 6,287,436 B1 | 9/2001 | Pelletier et al. |
| 6,324,438 B1 | 11/2001 | Cormier et al. |
| 6,352,577 B1 | 3/2002 | Martin et al. |
| 6,377,661 B1 | 4/2002 | Guru et al. |
| 6,388,816 B2 | 5/2002 | Brown et al. |
| 6,396,902 B2 | 5/2002 | Tybinkowski et al. |

(Continued)

Primary Examiner—Jonathan Johnson
(74) Attorney, Agent, or Firm—Fay Sharpe Fagan Minnich & McKee; Brian E. Turung; Robert V. Vickers

(57) ABSTRACT

A micro-reactor that is formed from a plurality of metal foil layers that are shaped by use of lithographic techniques in specific shapes. The formed metal foils layers are stacked and aligned together and then connected together to form one or more portions of the micro-reactor.

30 Claims, 9 Drawing Sheets

U.S. PATENT DOCUMENTS

| | | |
|---|---|---|
| 6,409,072 B1 | 6/2002 | Breuer et al. |
| 6,484,776 B1 | 11/2002 | Meilunas et al. |
| 6,490,812 B1 | 12/2002 | Bennett et al. |
| 6,494,614 B1 | 12/2002 | Bennett et al. |
| 6,507,642 B2 | 1/2003 | Fujishige et al. |
| 6,526,123 B2 | 2/2003 | Ein-Gal |
| 6,527,890 B1 | 3/2003 | Huang et al. |
| 6,533,840 B2 | 3/2003 | Martin et al. |
| 6,537,506 B1 * | 3/2003 | Schwalbe et al. ........... 422/130 |
| 6,556,657 B1 | 4/2003 | Tybinkowski et al. |
| 6,561,208 B1 | 5/2003 | O'Connor et al. |
| 6,575,218 B1 | 6/2003 | Burns et al. |
| 6,587,742 B2 | 7/2003 | Manuel et al. |
| 6,592,696 B1 | 7/2003 | Burdon et al. |
| 6,643,302 B1 | 11/2003 | Nishikawa et al. |
| 6,645,432 B1 | 11/2003 | Anderson et al. |
| 6,654,656 B2 | 11/2003 | Kesavadas et al. |
| 6,672,502 B1 | 1/2004 | Paul et al. |
| 6,676,835 B2 | 1/2004 | O'Connor et al. |
| 6,692,700 B2 | 2/2004 | Handique |
| 6,695,044 B1 | 2/2004 | Symonds |
| 6,729,352 B2 | 5/2004 | O'Connor et al. |
| 2002/0009741 A1 | 1/2002 | Simpson et al. |
| 2002/0048644 A1 | 4/2002 | Han |
| 2002/0106311 A1 | 8/2002 | Golbig et al. |
| 2002/0119079 A1 | 8/2002 | Breuer et al. |
| 2002/0189530 A1 | 12/2002 | David |
| 2002/0195048 A1 | 12/2002 | David |
| 2002/0195052 A1 | 12/2002 | David |
| 2003/0027022 A1 | 2/2003 | Arana et al. |
| 2003/0083410 A1 | 5/2003 | Baur et al. |
| 2003/0091496 A1 | 5/2003 | Resasco et al. |
| 2003/0152488 A1 | 8/2003 | Tonkovich et al. |
| 2003/0158410 A1 | 8/2003 | Nickel et al. |
| 2003/0164118 A1 | 9/2003 | Nickel et al. |
| 2003/0180216 A1 | 9/2003 | TeGrotenhuis et al. |
| 2003/0204285 A1 | 10/2003 | Thomas et al. |
| 2003/0204286 A1 | 10/2003 | Thomas et al. |
| 2003/0223909 A1 | 12/2003 | Oberbeck et al. |
| 2003/0235272 A1 | 12/2003 | Appleby et al. |
| 2005/0082351 A1 | 4/2005 | Pinchot |

\* cited by examiner

MICRO-REACTOR FABRICATION

This invention generally relates to a miniaturized chemical processing apparatus, and more particularly to a chemical processing apparatus assembled from layers of materials having specific compositions and/or shapes for used in a variety of chemical and/or biological applications.

BACKGROUND OF INVENTION

The field of chemistry and biology continues to advance at a rapid pace. New chemical and biological agents are developed daily in laboratory settings. However, conventional processing equipment suffers from a number of disadvantages. It has long been recognized in the chemical industry that "scale up" from laboratory bench-scale to commercial production scale is difficult. Results achieved in the laboratory are often difficult to duplicate at production rates in production facilities. Methods of controlling and optimizing processes for producing such chemical and biological compounds are becoming better understood. The control of parameters such as temperature, pressure, mixing conditions, relative volumes of reactants, and uses of catalysts are also becoming better understood. Traditionally, newly discovered chemical and biological compounds and processes involving either the production of such compounds, or processes involving the use of such compounds, have initially been carried out in "bench-scale" environments. Promising chemicals, biological agents, or processes are ultimately produced in mass quantity by application to industrial-scale processes. However, problems are often encountered in scaling up the process from the laboratory to industrial-scale production.

Conventional chemical processing equipment typically holds a relatively large volume of materials and consequently has a relatively large volume to surface area ratio. As a result, different portions of the reactant materials contained within such equipment are exposed to different histories of conditions. In the case of a conventional tank reactor, for example, even when temperature conditions at the walls of the reactor are well controlled, the portions of the reactants that are not in close proximity to the walls of the reactor may experience different temperature histories, especially if a significant temperature gradient exists, which might occur if the chemical reaction is strongly exothermic. Rapid stirring of the reactants may reduce this temperature history difference, but will not eliminate it. As a result of the nonhomogeneous temperature history, different portions of the reactants may chemically react differently. Undesired reactions may occur in portions of the reactants that are exposed to histories of higher than desired temperatures. This may result in the production of undesired waste products, which may be hazardous and which must be properly disposed of. In extreme situations reaction rates may accelerate to uncontrollable levels, which may cause safety hazards, such as potential explosions. If, however, the volume to surface area ratio of the processing apparatus is substantially reduced, the degree of precision of control of homogeneity of temperature history of the reactants can be substantially improved.

Other common problems associated with moving from bench-scale production to industrial-scale production involve changes in process conditions between the bench-scale environment and the industrial environment. For instance, the temperature of the reactants in a beaker or flask in a laboratory is easier to keep constant than the temperature in a production tank having a capacity of hundreds of gallons, as is often the case in a chemical processing plant. In addition, high pressures and temperatures are easier to maintain in small laboratory sized vessels than in much larger vessels used for production scale operation. In many instances, it is cost prohibitive or not feasible to scale up a reaction vessel from a bench-scale environment to industrial-scale processes. Variations in other process conditions within a large tank are also more difficult to control, and frequently affect the quality and yield of the desired product.

Another aspect of laboratory development of processes to produce chemical or biological compounds is that often potentially dangerous chemicals are used to create the desired product. Fires and explosions in research laboratories and concomitant injury to personnel and property are well known risks, especially in the chemical research industry. The risks are not limited only to research, since industrial chemical or biological production facilities also may experience fires and explosions related to chemical production using dangerous chemicals. Often, due to the quantities of chemicals used in industrial-scale processes, such accidents are significantly more devastating in an industrial setting than similar accidents in a research setting.

The materials of construction of conventional chemical processing apparatus, such as steel and specialty iron alloys, furthermore may be subject to corrosion and wear, may have undesirable effects on catalytic activity, or may "poison" a catalyst.

It has been recognized that a high degree of flow turbulence enhances the ability to rapidly mix two or more reactants together. Rapid mixing is important for fast-acting chemical reactions. A high degree of turbulence is also known to enhance heat transfer. Thus, a structure having both a low volume to surface area ratio and a high degree of flow turbulence is particularly advantageous for precise control of chemical processing.

Recently, increased attention has been directed to the use of micro-reactors for both development and production of chemical and biological processes. These types of reactors offer several advantages. As stated above, the control of chemical processes within very small reactors is typically easier than the control of a similar process in a large-scale production tank. Once a reaction process has been developed and optimized in a micro-reactor, it can be scaled up to industrial production level by replicating the micro-reactors in sufficient quantity to achieve the required production output of the process. If such reactors can be fabricated in quantity, and for a modest cost, industrial quantities of a desired product can be manufactured with a capital expenditure equal to or even less than that of a traditional chemical production facility. An additional benefit is that because the volume of material in each individual reactor is small, the effect of an explosion or fire is minimized, and with proper design, an accident in one reactor can be prevented from propagating to other reactors.

The use of micro-reactors has also resulted in an increase in safety in laboratory settings. In the research setting, the use of micro-reactors generally results in less exposure to hazardous substances and conditions by research personnel than when using traditional "batch chemistry" equipment, which equipment typically requires the researcher to physically handle chemicals in a variety of glass containers, often in the presence of a heat source. An accident in such an environment is likely to increase the risk of exposure to hazardous chemicals, and cause damage to the laboratory. However, when using a micro-reactor, the micro-reactor is typically a self-contained unit that minimizes the researcher's potential exposure to chemical substances. When using a micro-reactor, the researcher is not required to physically manipulate containers of chemical materials to carry out a desired reaction. As such the micro-reactor can be located in an area that will protect the researcher from an accident that could result in a fire or explosion.

Another area in which micro-reactors offer an advantage over conventional chemical process development and production is in the mixing of reactants. A mixing channel of the proper scale encourages a laminar flow of the reactants within the channel and is readily achievable in a micro-reactor. Laminar flow can enhance mixing by diffusion, which can eliminate the need to expend energy to physically stir or agitate the reactants.

Micro reactors are particularly applicable to the pharmaceutical industry, which engages in chemical research on many new chemical compounds every year, in the effort to find drugs or chemical compounds with desirable and commercially valuable properties. Enhancing the safety and efficiency of such research is valuable. When coupled with the potential that micro-reactors offer for eliminating the problems of moving from bench-scale production to industrial production, it is apparent that a micro-reactor suitable for use in carrying out a variety of chemical processes, and having an efficient and low cost design is desirable.

Several different designs for micro-reactors have been developed. Some of these designs are disclosed in U.S. Pat. Nos. 3,701,619; 5,534,328; 5,580,523; 5,690,763; 5,961,932; and U.S. patent application Ser. Nos. 2002/0106311 published Aug. 8, 2002, 2002/0048644 published Apr. 25, 2002; and 2003/0091496 published May 15, 2003. All of these patents and patent applications are incorporated herein by reference for teachings concerning reactors, materials used to manufacture the reactors, techniques used to manufacture the reactors, and catalysts used in association with the reactors.

One example of a micro-reactor is disclosed in U.S. Pat. Nos. 5,534,328 and 5,690,763, both of which are incorporated herein by reference. These two patents describe reactor structures for chemical manufacturing and production, fabricated from a plurality of interconnected layers. Generally, each layer has at least one channel or groove formed in it and most include orifices that serve to connect one layer in fluid communication with another. These layers are preferably made from silicon wafers, because silicon is relatively inert to the chemicals that may be processed in the reactor, and because the techniques required to mass produce silicon wafers that have had the required channels and other features etched into their surfaces are well known. A disadvantage of the micro-reactors described in the two patents stems from the rather expensive and complicated process required for manufacturing the devices. While silicon wafer technology has advanced to the state that wafers having desired surface features can readily be mass produced, the equipment required is capital intensive, and unless unit production is extremely high, the substantial costs are difficult to offset. While the two patents suggests that other materials can be used to fabricate the layers, such as metal, glass, or plastic, the surface features required (grooves, channels, etc.) must still be formed in the selected material. The specific surface features taught by the two patents require significant manufacturing steps to fabricate. For instance, while forming an opening through a material is relatively easy, forming a groove or channel that penetrates only part way through the material comprising a layer is more difficult, as the manufacturing process must not only control the size of the surface feature, but the depth as well. When forming an opening that completely penetrates through a material comprising a layer, depth control does not need to be so precisely controlled. The two patents teach that both openings which completely penetrate the layers, and surface features (grooves/channels) that do not completely penetrate the individual layers are required. Hence, multiple processing steps must be employed in the fabrication of each layer, regardless of the material selected.

U.S. Pat. No. 5,580,523, which is incorporated herein by reference, describes a modular micro-reactor that includes a series of modules connected in fluid communication, each module having a particular function (fluid flow handling and control, mixing, chemical processing, chemical separation, etc.). The patent teaches that the plurality of modules are mounted laterally on a support structure, and not stacked. In a preferred embodiment of the invention, silicon wafer technology is again used to etch channels and/or other features into the surface of a silicon wafer. Other disclosed fabrication techniques include injection molding, casting, and micro-machining of metals and semiconductor substrates. Again, the processing required to fabricate the individual modules goes beyond merely forming a plurality of openings into each component. Furthermore, the lateral layout of the reactor described in the patent requires a larger footprint (Basis Area) than a stacked plate reactor. The reactor requires more modules, thus a larger footprint of the entire reactor is required. In contrast, when additional plates are added to a stacked plate reactor, the footprint of the reactor does not change, which can be a distinct advantage, as in many work environments, the area an apparatus occupies on a workbench or floor is more valuable than the vertical height of the apparatus. As such, the disclosed reactor does not minimize the footprints and still provides flexibility to add components to customize the reactor for a particular process or application.

U.S. Pat. No. 5,961,932, which is incorporated herein by reference, discloses a reactor that is formed from a plurality of ceramic layers, which are connected in fluid communication, and wherein at least one layer includes a permeable partition. In the preferred embodiment, the patent describes that channels and passageways are formed in each layer. The particular process involves fabricating the layers from "green" or uncured ceramic, which once shaped as desired, must be sintered. The sintering process changes the size of the ceramic layer so that the sizes of the features formed into the ceramic layer in the initial stages of production are different than in the finished product. One problem with this reactor design is that the dimensions of the individual components cannot be rigidly controlled during fabrication since the components shrink. Such shrinkage can negatively effect the dimensions of the finished reactor. As such, precise dimensional control of fluid pathways in the reactor are difficult to maintain to achieve the desired flow rates through the reactor.

In U.S. patent application Ser. No. 2002/0106311 published Aug. 8, 2002 entitled "Enhancing Fluid Flow in a Stacked Plate Microreactor," which is incorporated herein by reference, a stacked plate chemical reactor in which simple plates are stacked together to form the reactor is disclosed. The stacked plates include openings that define fluid pathways and processing volumes within the stacked plates. In a preferred embodiment, an n-fold internal array is achieved by providing a first group of simple plates defining a reaction unit that includes bypass fluid channels and reaction fluid channels for each reactant, such that a portion of each reactant is directed to subsequent groups of simple plates defining additional reaction units. A chemical reactor with variable output is obtained by reversibly joining reactor stacks comprising irreversibly joined reaction units, these reaction units consisting of a plurality of simple plates. Other embodiments disclosed in the patent application employ at least one of an array of parallel fluid channels having different widths, bifurcated fluid distribution channels to achieve a substantially even flow equipartition for fluids with varying viscosities flowing within the fluid channels of each reaction unit.

In several of the prior art reactors identified above, relatively complicated manufacturing techniques are required. The manufacture of layers of silicon material requires a large capital investment. Sintering of a ceramic material requires the precise control of the shrinkage process, or individual components of a desired size cannot be achieved. In all cases, these reactors require complicated structures (for example, fluid channels and reaction channels) to be etched or otherwise fabricated in each layer. Additionally, orifices or passages also need to be formed in each layer, so that fluids can move between adjacent layers of the reactor. Thus, a series of different manufacturing steps typically must be performed for each layer. As such, it is desirable to provide a reactor design offering the advantages described above, which is relatively simple to manufacture, so as to minimize capital investment in scaling up production from the laboratory to the industrial production levels.

While a single micro-reactor can produce only a limited volume of product, additional micro-reactors can be added in parallel to increase production capacity. When additional modular micro-reactor units are added, additional systems for reactant supply, heat transfer media supply, and product collection are typically required, which not only increases the complexity of the system, but also requires more space for duplicative fluid systems. Furthermore, even minor differences in feed rates for some of the duplicate reactor modules can negatively effect product quality. Finally, more sophisticated control and monitoring are required to manage additional reaction modules and feed systems. It would therefore be desirable to provide a micro-reactor capable of n-fold parallelization without requiring that additional fluid and control systems be provided.

In an array of identical fluid channels having a single common reactant distribution channel and a single common product collection channel, with the reactant inlet and the product outlet located at opposite ends, where the common reactant distribution and the common product collection channel have the same cross sectional area, if the viscosity of the product relative to the reactants is substantially the same, then the pressure drop through the array can be considered the same, and the resulting flow distribution is fairly even, with only slightly lower flow rates in the central fluid channels. However, the flow distribution through such an array is not even if the viscosity of the product is significantly different than the viscosities of the reactants. When such an array is employed to process a reaction whose product has a significantly different viscosity compared to the viscosity of the mixture of the unreacted reactants, broad residence time distributions result in the array due to the fact that the pressure drop in the common reactant distribution channel no longer balances with the pressure drop in the common product collection channel. The flow rates within each individual fluid channel in the array are no longer identical. If the viscosity of the product is significantly greater than the viscosity of the mixed but unreacted reactants, then the flow rates in the individual fluid channels in the array tend to increase across the array for channels closest to the common product outlet. Thus the highest flow rate is experienced in the fluid channel in the array that is closest to the common product outlet, while the lowest flow rate is experienced in the fluid channel in the array that is located furthest from the common product outlet. This phenomenon is different if the viscosity of the product is less than the viscosity of the mixed but unreacted reactants. Thus for lower viscosity products, the highest flow rate is experienced in the fluid channel in the array that is closest to the common reactant inlet, while the lowest flow rate is experienced in the fluid channel in the array that is located furthest from the common reactant inlet. The greater the relative change in viscosity, the greater the variation in flow rates across the array. This imbalance leads to different residence times being associated with different fluid channels, resulting in an undesirable residence time distribution within the whole reaction unit. In certain cases, the additional residence time can lead to undesired cross reactions, and even clogging of the "slowest" fluid channels. As such, it is desirable to provide a micro-reactor including a plurality of fluid channels that is capable of processing reactant mixtures undergoing a significant viscosity change without the above-described residence time distributions and related problems.

For the specific residence time distributions discussed above, relative to reactant mixtures produced in fluid channels in which a plurality of different reactants are mixed, only one type of undesirable residence time distribution is of concern. Residence time distribution problems of this type can also arise in fluid channels used to direct reactants before mixing, as well as products for collection. It is desirable to provide a micro-reactor that includes a plurality of fluid channels adapted to provide substantially equal residence time distributions for fluid flow within the micro-reactor.

Computer modeling of reactors has increased in popularity due to increased computer processing power and increased sophistication in modeling software. As such, reactors are commonly modeled to have increased complexity (e.g., various passageway configurations for increased reactor residence time; passageway configurations to maintained desired flow patterns, temperature profiles, pressure profiles, etc.). These complex reactor designs are difficult, if not impossible, to manufacture and/or are cost prohibitive to manufacture by use of prior art reactor design techniques. Many chemical manufacturing processes also require exposure to catalytic materials to complete the chemical process. Precious metals such as gold, platinum, palladium, iridium, rhodium, silver and the like are used as catalysts in various chemical reactions. In the past, separate reactors had to be produced that contained each different catalyst material. The use of a plurality of reactors resulted in an increase in cost and complexity of a chemical reactor system.

As a result, there is a need for a micro-reactor that can be economically manufactured, can incorporate unique and sophisticated flow patters through the reactor, can maintain a desired relatively narrow temperature range for a process, has a relatively modest footprint, can provide desired diffusion mixing, can process reaction mixtures that form a product with different viscosities, can provide desired residence time distributions for fluid flow within the micro-reactor, and can include different types of catalytic materials.

SUMMARY OF THE INVENTION

The present invention pertains to a method for manufacturing a micro-reactor for use in the reaction of specialty chemicals for the pharmaceutical industry and will be described with particular reference thereto; however, the invention has much broader applications and the micro-reactor can be used in association with a wide variety of chemical reactions in the chemical, biological and/or pharmaceutical industry. In the specialty chemical industry (e.g., the pharmaceutical industry), relatively small amounts of chemical compounds are manufactured; however, larger reactor vessels are typically used to form these chemicals. Consequently, it is not uncommon for a reactor vessel to be running at 30% or less capacity. During the manufacture of many types of specialty chemicals, catalysts are commonly used to promote the reaction of the chemicals. Commonly, one or more precious metals such as, but not limited to, gold, platinum, palladium, iridium, rhodium, ruthenium, and/or silver, are used as catalysts. Each different precious metal used as a catalyst is typically placed in a separate reactor so that the precious metal can be later recovered after the catalyst has been spent. The use of multiple types of catalysts, each of which are placed in large reactor vessel, commonly results in a large capital expenditure on equipment that is only partially used for the formation of a particular chemical. In addition to the inefficient use of large reactor vessels during the manufacture of specialty chemicals, the use of large reactor vessels makes it difficult to maintain and/or control the required reaction parameters (e.g., reaction temperature, pressure, mixing rates, flow rates, etc.). The micro-reactor of the present invention is designed to overcome these shortcomings of past reactors. The micro-reactor of the present invention has a modular design having a top or front portion, a middle portion, and a bottom or back portion. The top or front portion of the micro-reactor is designed to be secured to one or more pipes, tubes or the like that feed the reactants to the micro-reactor. As can be appreciated, the reactants are typically in liquid and/or gas form; however, solid reactants can be used. The bottom or back portion of the micro-reactor is designed to be secured to one or more pipes, tubes or the like that direct the reacted reactants from the micro-reactor. Typically the top or front portion and bottom or back portion of the micro-reactor do not contain a catalyst when a catalyst is used in the micro-reactor; however, a catalyst can be positioned in and/or formed in the top or front portion and bottom or back portion of the micro-reactor if so desired. Typically the top or front portion and bottom or back portion of the micro-reactor are made of similar materials; however, this is not required. The middle portion of the micro-reactor typically includes one or more catalysts, when a catalyst is used in the micro-reactor.

In one aspect of the present invention, the micro-reactor has a modular design. The modular design of micro-reactor enables the components of the micro-reactor to be better costumed for a particular application. For instance, if a micro-reactor was required to handle a flow rate of A liter and be exposed to a catalyst B for a period of time C, a top or front portion and a bottom or back portion of the micro-reactor would be selected to handle flow rate A and a middle portion that includes or is made of catalyst B and having a sufficient surface area to achieve a time of exposure C would be selected. These three components would then be secured together to form the micro-reactor. If however, a micro-reactor was required to handle a flow rate of A liter and be exposed to a catalyst D for a period of time E, the same top or front portion and a bottom or back portion used in the previous micro-reactor could be used and a different middle portion that includes or is made of catalyst D and having a sufficient surface area to achieve a time of exposure E would then be selected. As such, the modular design of the micro-reactor increases the versatility of uses for the micro-reactor. In one embodiment of the invention, the top or front portion and/or the bottom or back portion of the micro-reactor are standardized for broad flow rate ranges and the middle portion is customized to achieve the desired flow rate and resident times in the middle portion. In this particular embodiment, the number of different components for the top or front portion and the bottom or back portion is reduced so as to reduce the cost of the modular micro-reactor. For instance, three sets of top or front portions and bottom or back portions could be used wherein set A can handle liquid flow rates of up to 1 liter per minute, set B can handle liquid flow rates of up to 10 liter per minute, and set C can handle liquid flow rates of up to 100 liter per minute. As can be appreciated, these are merely exemplary flow rate ratings and the one of more sets can have different flow rate ratings. Continuing with the example, if a micro-reactor was to be used to handle liquid flow rates of 15–25 liters per minute, set B would be selected for use in the reactor and a custom middle portion would then be selected that includes passage sizes that would limit the flow rate of liquid through the middle portion to close to about 25 liters per minute. In another example, if a micro-reactor was to be used to handle liquid flow rates of 50–75 liters per minute, set B would again be selected for use in the reactor and a custom middle portion would then be selected that includes passage sizes that would limit the flow rate of liquid through the middle portion to close to about 75 liters per minute. In still another example, if a micro-reactor was to be used to handle liquid flow rates of 0.5 liters per minute, set A would be selected for use in the reactor and a custom middle portion would then be selected that includes passage sizes that would limit the flow rate of liquid through the middle portion to close to about 0.5 liters per minute. As can be appreciated from these examples, a few standard sets of top or front portions and bottom or back portions can be manufactured for use in a wide variety of micro-reactor designs. In another and/or alternative embodiment, the size and shape of the passageways of one or more of the portions can be selected to achieve a desire flow profile (e.g. laminar flow, turbulent flow, etc.). The type of flow profile can be used to affect the mixing rates of the reactants and/or reaction rate of the reactants. The number of passageways, the size of the passageways at various points along the length of the passageway, and/or the shape of the passageway can be selected to achieve a desire flow profile. Typically the maximum diameter of the passageway is about 10–5000 micrometers; however, other sizes can be used. As can be appreciated, the maximum diameter of a passageway and/or shape of the passageway can be varied along the length of the passageway.

In another and/or alternative embodiment of the present invention, the top or front portion and bottom or back portion of the micro-reactor are made of a durable material. The materials are typically selected to be non-reactive with the materials passing through the micro-reactor. The materials are also typically selected to handle the temperatures and pressures of the materials passing through the micro-reactor. In one embodiment, the materials include crystalline materials, ceramics, glasses, polymers, composite materials, and/or metals. In one embodiment, the top or front portion and bottom or back portion of the micro-reactor are made of metals such as, but not limited to, stainless steel, nickel, nickel alloys, titanium, titanium alloys, aluminum, and aluminum alloys.

In still another and/or alternative embodiment of the present invention, the middle portion of the micro-reactor includes a catalyst. In many chemical reactions, a catalyst is required to promote the reaction of one or more reactants. In systems that require a catalyst, the micro-reactor includes one or more catalysts. Typically the catalyst is located in the middle portion of the micro-reactor; however, the catalyst can be located in other or additional locations in the micro-reactor. In one embodiment of the invention, the micro-reactor includes a single metal catalyst in one or more portions of the micro-reactor. The catalyst can be formed in the micro-reactor and/or inserted in one or more regions of the micro-reactor. In another and/or additional embodiment of the invention, the micro-reactor includes a plurality of metal catalysts in one or more portions of the micro-reactor. One or more of the catalysts can be formed in the micro-reactor and/or inserted in one or more regions of the micro-reactor. In one non-limiting aspect of this embodiment, the metal catalyst is attached to or formed on the wall of one or more passageways in one or more portions of the micro-reactor. In one specific example, the walls of the passageways include the metal catalyst. In another and/or alternative non-limiting aspect of this embodiment, two metal catalysts are attached to or formed on the wall of one or more passageways in one or more portions of the micro-reactor. In one specific example, one portion of the walls of the passageways includes one metal catalyst and another portion of the walls of the passageways includes the other metal catalyst.

In yet another and/or alternative embodiment of the present invention, the middle portion includes one or more passageways used to facilitate in the desired reaction of the chemical reactants. Various parameters are used to control a chemical reaction. Such parameters include temperature, pressure, flow rate, and/or surface area of catalyst exposure. The size of the passageways through the middle portion of the micro-reactor can be selected to affect the flow rate and/or pressure of the reactants as the reactants pass through the middle portion. The length and/or configuration of the passageways can be selected to obtain the amount of time of catalyst exposure, especially when the passageways include the catalyst.

In still yet another and/or alternative embodiment of the present invention, the micro-reactor includes one or more passageways used to obtain a desired temperature profile for the micro-reactor. One or more portions of the micro-reactor can include one or more passageways to allow a heating or cooling fluid to flow to thereby regulate the temperature of one or more of the reactants in the micro-reactor. Alternatively or additionally, one or more heating elements (e.g., heating coil, etc.) can be incorporated in one or more of the portions of the micro-reactor to regulate the temperature of one or more of the reactants in the micro-reactor. One or more temperature sensors can be incorporated in one or more of the portions of the micro-reactor to facilitate in the control of the temperature in the micro-reactor.

In a further and/or alternative embodiment of the present invention, one or more portions of the micro-reactor are connected together in a manner that allows for later disconnection. The separation of the portions of the micro-reactor is advantageous when one or more portions of an unused module can be used to form another micro-reactor. As such, the portions of the micro-reactor can be recycled and reused in other micro-reactors, thereby reducing waste and extending the life of one or more portions of the micro-reactor. The separation of the portions of the micro-reactor is also advantageous when the spent or partially spent catalyst in one or more portions of the micro-reactor is to be recovered. When valuable or precious metals are used as the catalyst, the recovery of such metals is desirable. In the past, the full reactor that included the catalyst was melted down in order to recover the desired metal catalyst. The micro-reactor of the present invention can be designed such that one or more portions of the micro-reactor includes the catalyst. As such, when the micro-reactor is taken out of service, the micro-reactor can be taken apart and the portion containing the catalyst can be removed for recovery of the catalyst. If the micro-reactor includes two or more different catalysts, the portions containing the different catalyst can be separated and then processed in separate recovery processes thereby minimizing contamination of the recovered catalyst. In prior micro-reactor designs, different catalysts were not placed in the same micro-reactor since during recovery of the catalyst, which was typically accomplished by melting the catalyst, the inclusion of two or more catalysts would result in the contamination of the catalysts (e.g. alloying of the catalysts) and/or required added steps to separate out the different catalyst resulting in additional time, complexity and cost. The modular configuration of the micro-reactor of the present invention overcomes this past deficiency of prior art reactors and allows a micro-reactor to be formed having a plurality of different catalysts, which micro-reactor can be later disassembled and the catalysts separated for separate recovery operations. In one embodiment, two or more portions of the micro-reactor are held together by an applied compressive force. When a compressive force is used (e.g., clamps, bolts, etc.), the contact surfaces of the portions of the micro-reactor are generally smooth to increase the seal between the contact surfaces. Typically, the roughness of the contact surfaces is less than about one (1) micrometer, and substantially free of scratches. The pressure used to secure the plates together will vary depending on the pressure in the micro-reactor, among other factors. Sealing structures such as, but not limited to, o-rings and sealing rings can be used to further enhance the seal between contact surfaces. In another and/or alternative embodiment, two or more portions of the micro-reactor are connected together by brazing. The brazing metal will have a melting point that is less than the metal composition of the portions of the micro-reactor being connected together, will be substantially insert to the reactant passing through the micro-reactor, and will be able to withstand the temperature and pressures in the micro-reactor. For instance, if the micro-reactor includes three components, namely a top portion, a bottom portion and a middle portion, and the contact surfaces of the top and bottom portion is made of stainless steel and the middle portion is primarily made of palladium, a brazing metal would be selected to have a melting point that is less than the melting point of palladium. Palladium has a melting point (1554° C.) that is less than stainless steel (~2500° C.). As such, during a brazing process, the middle portion that is formed of palladium is most susceptible to damage. By selecting a brazing metal that is less than the melting point of palladium, the brazing operation for connecting the components together will not damage any of the portions of the micro-reactor. Typically the metaling point of the brazing metal is at least about 100° C. less than the lowest melting temperature contact surface, and more typically at least about 200° C. less than the lowest melting temperature contact surface, and even more typically at least about 300° C. less than the lowest melting temperature contact surface. One non-limiting brazing metal than can be used is a nickel-silver alloy which typically has a melting point of less than about 1000° C. The brazing metal can be applied to the contact surfaces of the portions of the micro-reactor by plating, metal spraying, hot dipping or other type of operation. The heating of the brazing material can occur in an oven, by induction heating, by lasers, etc. When the portions of the micro-reactor are to be separated, the brazing metal is reheated until it softens or becomes molten and the portions are then separated from one another. The spent or partially spent palladium catalyst in the middle portion can then be processed and recovered. The top and bottom portions of the micro-reactor can be discarded or cleaned and reused to form another micro-reactor.

In still another and/or alternative embodiment, an adhesive is used to connect one or more portions of the micro-reactor. When the time has come to recover the catalyst, a solvent can be used to dissolve the adhesive and enable separation of the portions of the micro-reactor. Many different types of adhesives can be used.

In still a further and/or alternative embodiment of the present invention, at least one portion of the micro-reactor is formed from a plurality of metal foil layers. The method of manufacturing the micro-reactor or one or more portions of the micro-reactor includes 1) generating a computer image of the micro-reactor or the one or more portions of the micro-reactor, 2) sectioning the computer generated image, 3) forming sections of the micro-reactor or the one or more portions of the micro-reactor from a metal material based on each of the drawing sections, and 4) connecting the individual sections to form the micro-reactor or the one or more portions of the micro-reactor that substantially matches the computer generated drawing of the micro-reactor or the one or more portions of the micro-reactor. By using this novel manufacturing technique, micro-reactor or the one or more portions of the micro-reactor has very precise dimensions that can be manufactured having very low error tolerances. In one embodiment of the invention, the computer drawing of the micro-reactor or the one or more portions of the micro-reactor can be generated by commercially available or proprietary software. One common commercial software package is AutoCAD. Many other software packages can be used. The computer drawing is at least a two dimensional drawing and typically a three dimensional drawing of the micro-reactor or the one or more portions of the micro-reactor. Once the computer generated drawing matches the shape of the micro-reactor or the one or more portions of the micro-reactor, the drawing is then sectioned to emulate layers of the micro-reactor or the one or more portions of the micro-reactor. Typically, the layers are divided or sectioned along the longitudinal axis or vertical axis of the micro-reactor or the one or more portions of the micro-reactor; however, graphics of the micro-reactor or the one or more portions of the micro-reactor can be divided along other axes of the micro-reactor or the one or more portions of the micro-reactor can be used. The divided or sectioned layers typically have the same thickness, however, this is not required. The computer generated images for the micro-reactor or the one or more portions of the micro-reactor can be saved, used in other processes (e.g., lithography process, etc.) or the like. In still another and/or alternative embodiment of the invention, the divided or sectioned layers of the micro-reactor or the one or more portions of the micro-reactor are formed from a metal material that matches which low error tolerances. Various techniques can be used to produce the divided or sectioned layers of the micro-reactor or the one or more portions of the micro-reactor. In one aspect of this embodiment, lithography is used to at least partially form one or more divided or sectioned layers of the micro-reactor or the one or more portions of the micro-reactor. When using a lithography process, a photo-sensitive resist material coating is applied to one or more of the surfaces (i.e., either of the relatively large planar "top" or "bottom" surfaces) of a blank of metal material (e.g. metal foil, etc.). After the blank has been provided with the photo-resist material coating, "mask tools" or "negatives" or "negative masks", containing a positive or negative image of the desired sectioned layer of the micro-reactor or the one or more portions of the micro-reactor are etched in the blank. The mask tools can be made from glass or other materials, which has a relatively low thermal expansion coefficient and transmit radiation such as ultraviolet light. The blank is then exposed to radiation, typically in the form of ultraviolet light, to expose the photo-resist coatings to the radiation. The masks are then removed and a developer solution is applied to the surfaces of the blank to develop the exposed (sensitized) photo-resist material. Once the photo-resist is developed, the blanks are etched or micro-machined. Once etching or machining is complete, the remaining unsensitized photo-resist material can be removed such as by, but not limited to, a chemical stripping solution. When using lithography as a basis for layer fabrication of the sectioned layers, parts and/or features of the micro-reactor or the one or more portions of the micro-reactor can be designed as diameters, squares, rectangles, hexagons, and/or any other shape and/or combination of shapes. The combinations of any number of shapes can result in non-redundant design arrays (i.e. patterns in which not all shapes, sizes, and/or spacings are identical). Lithographic features can represent solid or through aspects of the final micro-reactor or final portion of the micro-reactor. Such feature designs can be useful for fabricating micro-structures, surfaces, and/or any other structure that can employ a redundant and/or non-redundant design for certain micro-structural aspects. Large area, dense arrays can be produced through the lithographic process, thereby enabling creation of devices with sub-features or the production of multiple devices in a batch format. Lithography can also allow the creation of very accurate feature tolerances since those features can be derived from a potentially high-resolution photographic mask. The tolerance accuracy can include line-width resolution and/or positional accuracy of the plotted features over the desired area. Photographic masks can assist with achieving high accuracy when chemical or ion-etched, or deposition-processed layers are being used to form a micro-reactor or the one or more portions of the micro-reactor from the stack of sections. Because dimensional changes can occur during the final formation of the micro-reactor or the one or more portions of the micro-reactor, compensation factors can be engineered at the photo-mask stage, which can be transferred into the fabrication of the micro-reactor or the one or more portions of the micro-reactor. For instance, when the micro-reactor or the one or more portions of the micro-reactor needs to be angled for radial designs or some other design, the photo-mask typically needs to be applied to both sides of the metal foil layer with a slight offset to allow for the angle. This offset will eliminate a stack-up look even though the steps will be very thin. When the brazing material is coated on both sides of every other metal foil layer, the etching solution typically performs a better job to form a better angled stack. In another and/or alterative aspect of this embodiment, fabricating the sections of the micro-reactor or the one or more portions of the micro-reactor can be formed by one or more micro-machining techniques. Some of the micro-machining techniques that can be used include, but are not limited to, photo-etching, laser machining, reactive ion etching, electroplating, vapor deposition, bulk micro-machining, surface micro-machining, and/or conventional machining. Ion etching techniques can form sectioned layers of the micro-reactor or the one or more portions of the micro-reactor that have tolerances of less than about 1.25 microns. Photo-chemical-machining techniques can etched a sectioned layers of the micro-reactor or the one or more portions of the micro-reactor to tolerances of less than about 2.5 microns or about 10% of the metal thickness. Laser micromachining techniques can produce a sectioned layer of the micro-reactor or the one or more portions of the micro-reactor to a tolerance of less than about 0.3 micron. Electroforming techniques can produce sectioned layer of the micro-reactor or the one or more portions of the micro-reactor to a tolerance of less than about 0.1 micron. In yet another and/or alternative embodiment of the invention, one or more sectioned layers of the micro-reactor or the one or more portions of the micro-reactor are connected together by a lamination process. Once the multiple sectioned layers of the micro-reactor or the one or more portions of the micro-reactor are formed in the metal material, the sections are placed together to define the desired the micro-reactor or portion of the micro-reactor. The total number (and thickness) of the sectioned layers of the micro-reactor or the one or more portions of the micro-reactor define the overall height and aspect ratio of the micro-reactor or the one or more portions of the micro-reactor. In one embodiment, a metal-to-metal brazing technique is used to connect together one or more sectioned layers of the micro-reactor or the one or more portions of the micro-reactor. Prior to the assembly of the sectioned layers of the micro-reactor or the one or more portions of the micro-reactor, one or more sectioned layers of the micro-reactor or the one or more portions of the micro-reactor can have one or both surfaces coated with a thin metal layer. Such coating techniques can include, but are not limited to, thermal spraying and electroplating. Generally the thickness of the metal coating is less than about 10 microns and typically about 0.1–10 microns, and more typically about 0.5–4 microns. The coated metal should have a melting temperature that is less than the metal used to form the sectioned layers of the micro-reactor or the one or more portions of the micro-reactor. Typically the coating metal has an average melting point that is at least about 100° C. less than the average melting point of the metal used to form the sectioned layers of the micro-reactor or the one or more portions of the micro-reactor, and typically is at least about 300° C. less than the average melting point of the metal used to form the sectioned layers of the micro-reactor or the one or more portions of the micro-reactor. Examples of coating metal materials include, but are not limited to, nickel-silver alloys (e.g., BAg-3, BAg-4, BAg-7, BAg-13, BAg-22 etc.), nickel alloys (e.g., BNi-1, BNi-2, BNi-3, BNi-8, etc.), gold alloys (e.g., BAu-1, AAu-3, BAu-4, BAu-5, BAu-6, etc.), aluminum-silicon alloys (e.g., BAlSi-2, BAlSi-4, BAlSi-7(d), BAlSi-10(d), etc.), copper alloys (e.g., BCu-1, BCu-2, BCuP-1, etc.), and other various brazing alloys (e.g., 10PdAu, 95Ag-5Al, 9Pd-9Ga—Ag, 48Zr-48Ti-4Be, etc.). As can be appreciated, alloys of these metals and/or other metals can be used. During the brazing process, the sectioned layer assembly can be heated in an inert atmosphere to an elevated temperature to cause the metal coating to flow. The heating of the brazing metal can be achieved by use of induction heating, radiant heating, lasers, furnaces, ovens, torches, electrical resistance, dipping procedures, etc. Typically the brazing temperature is at least about 10° C. higher than the average melting point of the brazing metal and at least 100° C. less than the average melting point of the metal foil. The atmosphere about the micro-reactor sections or the one or more portions of the micro-reactor sections can be held under vacuum to result in a vacuum brazing process. The atmosphere is typically an inert atmosphere. Gas atmospheres that include hydrogen, nitrogen or noble gases can be used. The time of brazing is typically about 0.1–4 hours. The elevated temperature during brazing causes the brazing metal to flow between the metal foil layers. The brazing procedure is completed by cooling the sectioned layers of the micro-reactor or the one or more portions of the micro-reactor. The atmosphere during cooling is typically inert. The cooling times are typically 0.1–5 hours. As the temperatures elevate, the sectioned layers of the micro-reactor or the one or more portions of the micro-reactor can expand. Various types of alignment structures (e.g., pins, etc.) can be used to maintain the sectioned layers of the micro-reactor or the one or more portions of the micro-reactor in the proper position during the heating process. In one non-limiting embodiment, construction holes or slots are formed in each foil layer which are used to align the foil layers. The construction holes or slots can be sized and shaped to account for expansion and/or contraction of the foil layers when exposed to heat. Typically, each foil layer includes a plurality of construction holes or slots to facilitate in the proper orientation of the layer layers when forming the micro-reactor or the one or more portions of the micro-reactor. The pins can be made of the same material as the foil layers so that the pins expand and contact at the same rate as the foil layers when exposed to heating and cooling. Alternatively, the pins can be formed of carbon material (e.g. graphite) or other type of material that has little or no expansion during heating and cooling. The layers of metal foil can also be clamped together or otherwise placed under pressure to limit movement of the foil layers during the brazing process. In addition to using alignment structures, positional errors of the sectioned layers of the micro-reactor or the one or more portions of the micro-reactor (stacking errors) and tolerances can be controlled by the photographic masks used to produce the layers. The geometric size and tolerance of the sections can be partially controlled by the layer thickness and/or micro-machining methods used to produce the sections. When producing a laminated micro-reactor or laminated portion of the micro-reactor, numerous factors can be an influence on the overall tolerances of the sectioned layers. For example, when using a stacking fixture, the flatness of the laminating surface of the sectioned layers and the perpendicularity of the sides of the sectioned layers can be controlled. In addition, the dimensional tolerance of the alignment features of the sectioned layers and/or the positional tolerance of the sectioned layers can be an influence. In yet another and/or alterative embodiment of the invention, one or more layers of metal foil can be laminated together by use of an adhesive. Such adhesives can include, but are not limited to, thermo-cured epoxy, non-thermo-cured epoxy, silicone rubber products, urethanes, etc. When using lamination techniques other than brazing, the sectioned layers of the micro-reactor or the one or more portions of the micro-reactor are typically clamped together or otherwise placed under pressure until the adhesive has at least partially dried and/or cured. In still yet another and/or alternative embodiment of the invention, the metal sections of the micro-reactor or the one or more portions of the micro-reactor can be formed from a wide variety of metals. The metal foil can be made of a single metal or be a metal alloy. The micro-reactor or the one or more portions of the micro-reactor can be formed of the same of different metals. In one aspect of this embodiment, the top or front portion of the micro-reactor is formed a durable, non-precious metal. Such metals include, but are not limited to, stainless steel, nickel, nickel alloys, aluminum, aluminum alloys, titanium, titanium alloys. In another and/or alternative aspect of this embodiment, the bottom or back portion of the microreactor is formed a durable, non-precious metal. Such metals include, but are not limited to, stainless steel (e.g., 304, 316, etc.), nickel, nickel alloys (N02200, N02205, N02270, N04400, N06600, N08800, N10001, etc.) aluminum, aluminum alloys (1160, 1100, 1235, etc.), titanium, titanium alloys (Ti-0.3Mo-0.8Ni, Ti-6Al-4V, Ti-10V-2Fe-3Al, etc.). In still another and/or alternative aspect of this embodiment, the middle portion or a segment of the middle portion of the micro-reactor is formed a catalyst metal. Such metals include, but are not limited to, aluminum, cobalt, copper, gold, iridium, lithium, molybdenum, nickel, platinum, palladium, rhodium, ruthenium and/or silver. The metal foil layers can be made fully from a single metal or can be made of a plurality of metals. Alternatively or additionally, one or more segments of the middle portion can be made of one or more metal foil layers of one metal and one or more other segments can be made of one or more metal foil layers of another metal. If both of these metals are precious metals and/or recoverable metals, the section of the brazing metal can be selected to separate the segment of different metals without disturbing the bond between the metal foil layers of the same metal. For example, the middle portion of the micro-reactor is formed of two segments wherein each of the segments if formed of a different metal (e.g., segment A is formed layers of platinum and segment two is formed from layers of palladium). The brazing metal A' selected to connect the metal foil layers of section A and the brazing metal B' selected to connect the metal foil layers of section B can both be selected to have a higher melting point than the brazing metal C' selected to connect the two segments together. As a result, the middle section can be heated to the melting point of brazing metal C' and below the melting point of brazing metals A' and B' thus enabling the two segments to be separated from one another without resulting in the layers of the two segments separating from one another. The separated segments can then be cooled and sent to their respective recovery processes to recover the two different types of metal catalysts. In a further and/or alternative embodiment of the invention, the thickness of the metal foil layers is about 10–400 microns, and more typically about 40–150 microns. The thin thickness of the metal foil layers facilitates in the ease of processing the metal foil during the lithography process and also results in a higher quality final product. The non-limiting examples set forth above illustrate a process for manufacturing micro-reactors for the processing of chemicals and/or pharmaceuticals by strategically replacing certain leaves in the stack with very thin metal leaves of catalyst material. By flowing the reactants through these catalytic passages that are formed by offsetting the cells (or channels) in the metal foil layers, a desired catalytic reaction is achieved to form a desired product. The openings in the metal layers are offset from the edges of the metal layers to increase the strength of the formed middle portion. The manufacturing method of the present invention enables the formation of a micro-reactor having a small but intricate and complex three dimensional passageway system through the micro-reactor to achieve a high reaction surface area to strength ratio. The formed middle portion can then be encased in a durable structure and/or clamped together (e.g., toggle press or wedge clamp) to enable the reaction in the micro-reactor to safely occur at elevated pressures and temperatures beyond that of which can be achieved using the traditional cylindrical reactor vessels, plated ceramic catalyst beds and the ceramic honeycomb catalyst supports used in the chemical industry today. The manufacturing process for the micro-reactor of the present invention also enables the reactants to be exposed to multiple catalysts as the reactants passed through the micro-reactor. As a result, the micro-reactor eliminates the need for multiple reactor vessels in a refinery. Increasing chemical production by use of the micro-reactor of the present invention merely requires adding additional micro-reactors to the system. As a result, the micro-reactor eliminates the need of installing large vessel reactors online anticipating increased demand in the future (which large reactors results in under-utilization of the reactor). In addition, chemical processing by use of the micro-reactors is safer, cleaner, more accurate and efficient at the pressures and temperatures as compared to larger reactor vessels. Recovery of the catalyst, especially a precious metal catalyst, is much simpler in the micro-reactor of the present invention than melting the entire reactor down (when it becomes plugged or deficient) and separating the elements at their perspective melt and density points or using various highly toxic methods of reduction now in use at most of the catalyst producers (e.g., separating the precious metal from the ceramic supports). The method of recovery of the catalyst in the micro-reactor of the present invention is not only simpler and less costly, it is also much more environmentally friendly. Changeover of catalyst beds when using the micro-reactor of the present invention can be done unit by unit while still under processing conditions instead of shutting down whole reactor vessels to change out tons of catalyst.

A primary object of the present invention is a manufacturing process for a micro-reactor or one or more portions of a micro-reactor with high precision.

Another and/or alternative object of the present invention is a manufacturing process for a micro-reactor or one or more portions of a micro-reactor that includes the use of computer generated images and lithographic techniques to manufacture a manufacturing process for a micro-reactor or one or more portions of a micro-reactor.

Still another and/or alternative object of the present invention is a manufacturing process for a micro-reactor or one or more portions of a micro-reactor that includes the connecting of thin layers of dense metal to form the micro-reactor or one or more portions of the micro-reactor.

Yet another and/or alternative object of the present invention is a manufacturing process for a micro-reactor or one or more portions of a micro-reactor that includes vacuum brazing to connect together one or more sectioned layers of a micro-reactor or one or more portions of a micro-reactor.

Still yet another and/or alternative object of the present invention is a manufacturing process for a micro-reactor or one or more portions of a micro-reactor that includes a lithographic technique to form distinct shapes in a metal foil that is representative of a section of the micro-reactor or one or more portions of the micro-reactor.

A further and/or alternative object of the present invention is a manufacturing process for a micro-reactor or one or more portions of a micro-reactor that utilizes guide structures and holes or slots to properly align the foil layers to facilitate in the proper formation of the micro-reactor or one or more portions of the micro-reactor.

Still a further and/or alternative object of the present invention is a manufacturing process for a micro-reactor or one or more portions of a micro-reactor that includes coating one or more sides of a metal foil with a thin metal layer for use in brazing one or more metal foil layers together to form the micro-reactor or one or more portions of a micro-reactor.

Yet a further and/or alternative object of the present invention is a manufacturing process for a micro-reactor or one or more portions of a micro-reactor that can form the micro-reactor or one or more portions of a micro-reactor to have any desired simple or complex shape.

Still yet a further and/or alternative object of the present invention is a manufacturing process for a micro-reactor or one or more portions of a micro-reactor that enables one or more portions and/or sections of a portion of the micro-reactor to be easily connected and disconnected.

Another and/or alternative object of the present invention is a manufacturing process for a micro-reactor or one or more portions of a micro-reactor that enables simplified catalyst recovery.

Still another and/or alternative object of the present invention is a manufacturing process for a micro-reactor or one or more portions of a micro-reactor that enables multiple catalysts to be used and enables the multiple catalysts to be easily separated for separate recovery processes.

Yet another and/or alternative object of the present invention is a manufacturing process for a micro-reactor or one or more portions of a micro-reactor that allows for easier scalability of the micro-reactor from laboratory settings to industrial settings.

Still yet another and/or alternative object of the present invention is a manufacturing process for a micro-reactor or one or more portions of a micro-reactor that forms a durable micro-reactor that can withstand a large range of pressures and temperatures.

A further and/or alternative object of the present invention is a manufacturing process for a micro-reactor or one or more portions of a micro-reactor that can be formed by a modular design.

Still a further and/or alternative object of the present invention is a manufacturing process for a micro-reactor that is modular in design and has standardized components that can be used in forming a variety of different micro-reactors.

Yet a further and/or alternative object of the present invention is a manufacturing process for a micro-reactor that has a high surface area to strength ratio.

Still yet a further and/or alternative object of the present invention is a micro-reactor that simplifies the recovery of precious metal catalysts from the micro-reactor.

These and other objects and advantages will become apparent from the discussion of the distinction between the invention and the prior art and when considering the preferred embodiment as shown in the accompanying drawings.

BRIEF DESCRIPTION OF THE DRAWINGS

The foregoing objects, and others, will in part be obvious and in part pointed out more fully hereinafter in conjunction with the written description of preferred embodiments of the invention illustrated in the accompanying drawings in which.

DETAILED DESCRIPTION OF A PREFERRED EMBODIMENT

Figure 1:
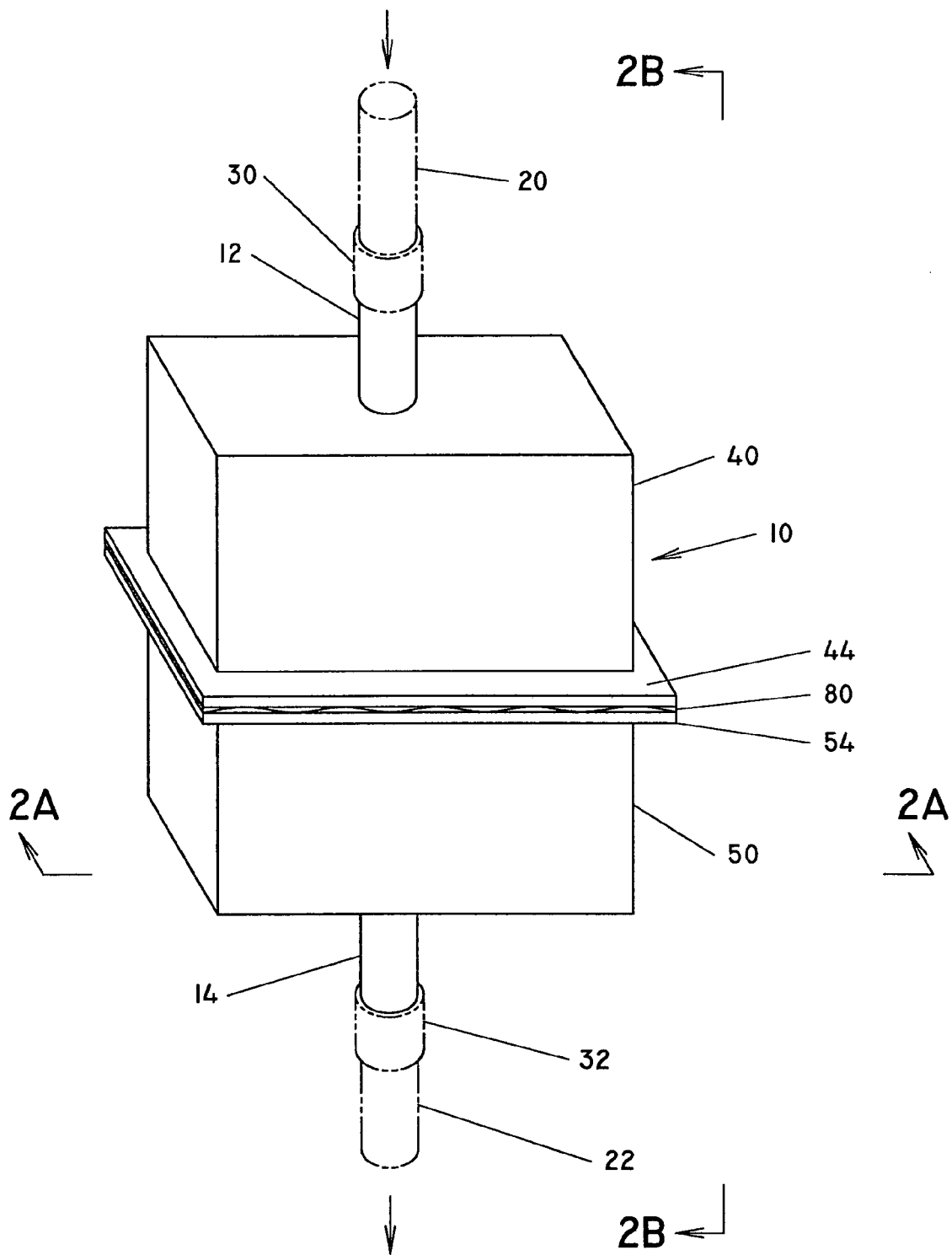
FIG. 1 is an elevation view of a micro-reactor of the present invention connected between two pipes.

Referring now in greater detail to the drawings, wherein the showings are for the purpose of illustrating preferred embodiments of the invention only and not for the purpose of limiting the invention, FIG. 1 illustrates a micro-reactor 10 connected between two pipes 20, 22. The arrows illustrate that one or more reactants enter the micro-reactor from pipe 20 and exit the micro-reactor by pipe 22. Micro-reactor 10 includes two connection extensions 12, 14 that are connected to pipes 20, 22 respectively by connectors 30, 32. Connectors 30, 32 can be any type of connector (e.g., connection sleeve, threaded pipe end, quick connector, etc.). As can be appreciated, pipe 20 and/or pipe 22 can be directly connected to the body of the micro-reactor. The micro-reactor is illustrated as having a generally rectangular cross-sectional shape; however, the micro-reactor bac have many of other shapes, such but not limited to, square, oval, circular, etc. The micro-reactor is also illustrated as having a generally uniform cross-sectional shape; however, the cross-sectional shape can be non-uniform along the longitudinal and/or lateral length of the micro-reactor. The micro-reactor typically has a size of about 1–12 inches long, about 0.5–6 inches wide and about 0.5–10 inches thick; however, other sizes of the micro-reactor can be formed.

The micro-reactor is designed such that one or more reactants (e.g. gas, liquid, solid particles, etc.) to be processed are introduced or flowed into the inlet of the micro-rector. The reactants in the micro-reactor are then subjected to desired temperatures, pressures, flow rates and/or catalysts to achieved the desired chemical reaction. One or more channels or passageways through the micro-reactor are formed to obtained the desired mixing rates, flow rates, heat exchange, and/or catalytic reactions of one or more of the reactants in the micro-reactor. After the reacted chemicals have passed through the micro-reactor, the reacted chemicals exit the outlet port of the micro-reactor and proceed to further processing or packaging. The micro-reactor of the present invention is particularly directed to the speciality chemical industry which includes pharmaceuticals; however, the micro-reactor can be used manufacture non-specialty chemicals.

Figure 2A:
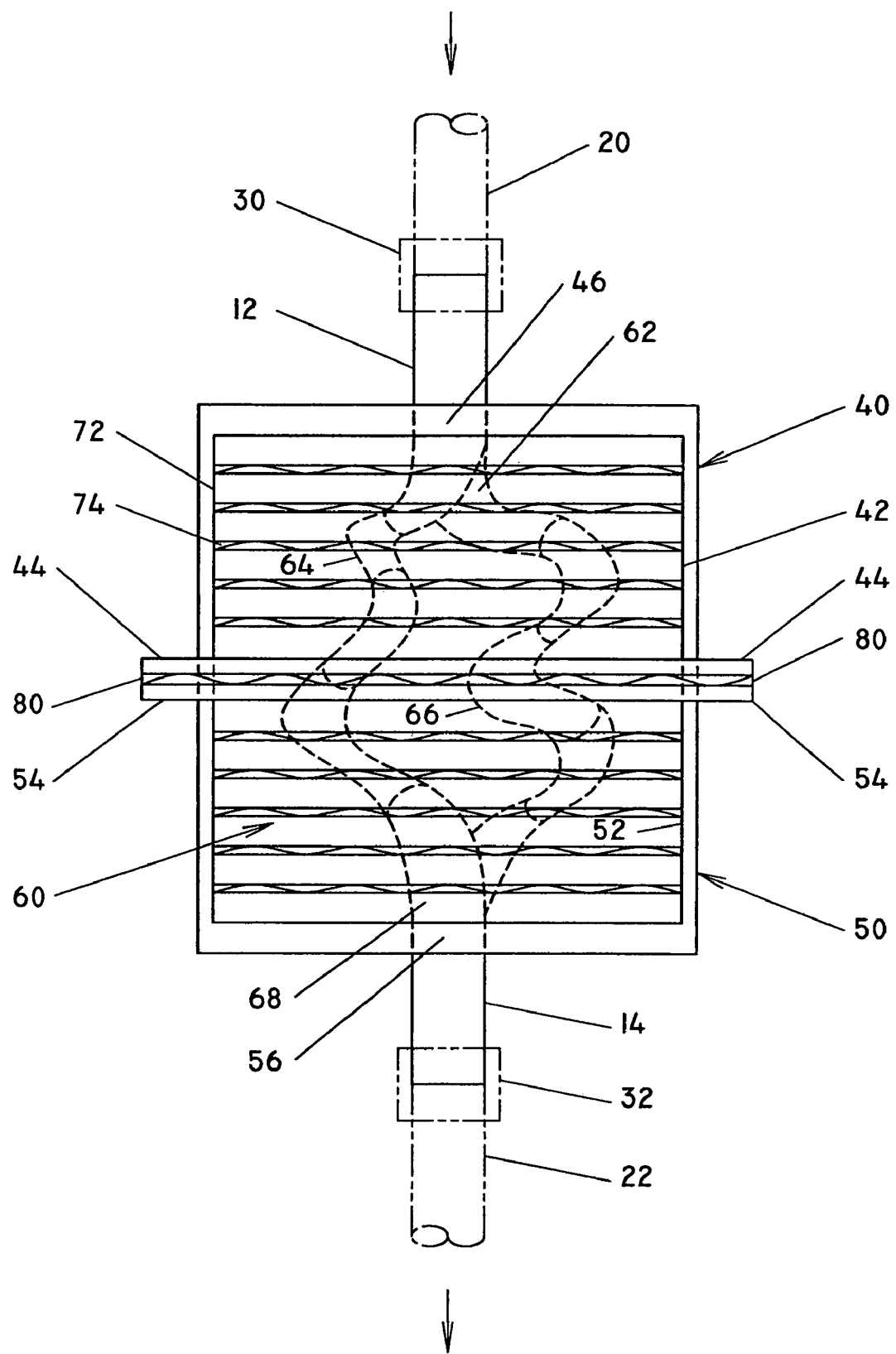
FIG. 2A is a cross-sectional view along lines 2A—2A of FIG. 1.
Figure 2B:
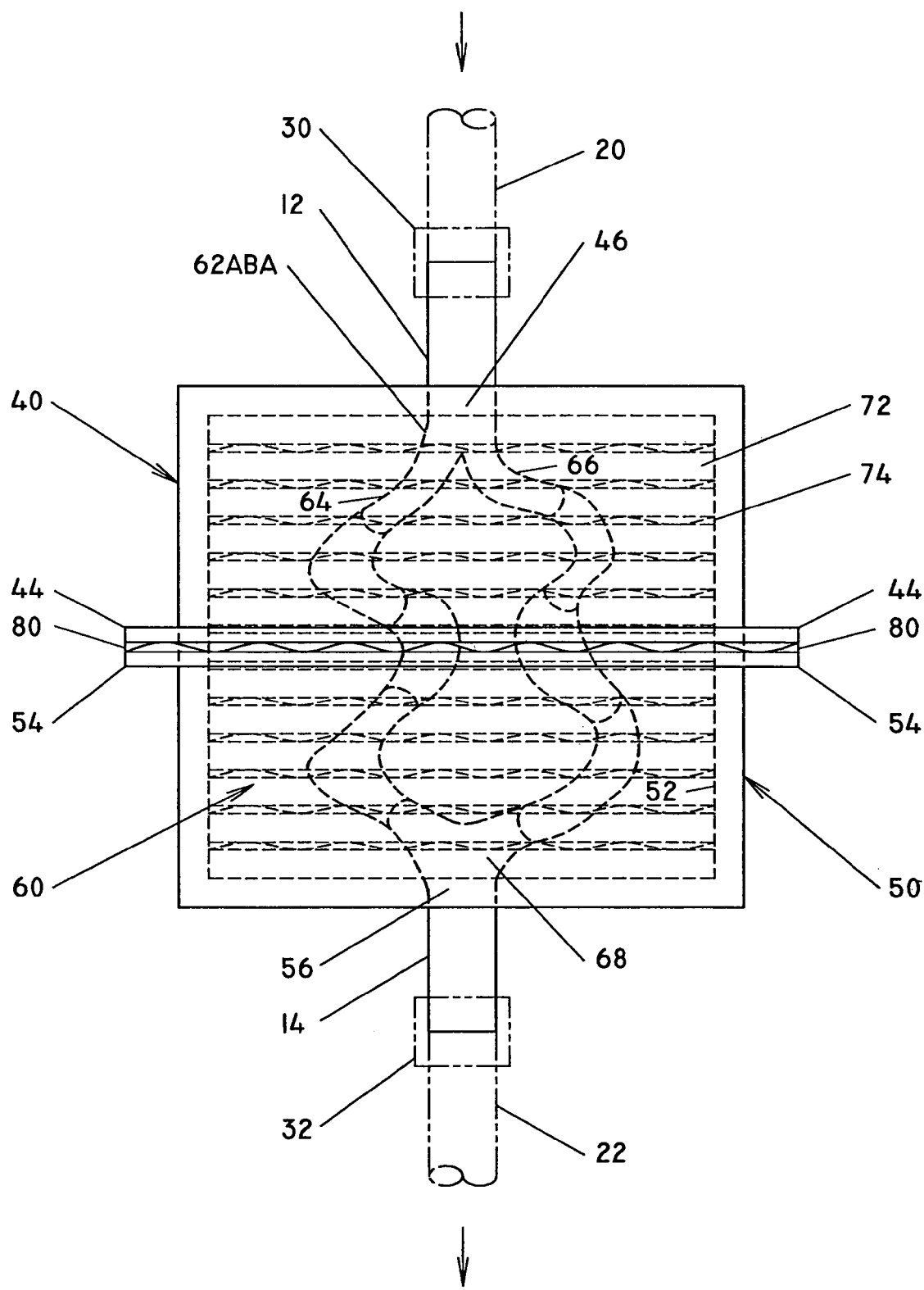
FIG. 2B is a cross-sectional view along lines 2B—2B of FIG. 1.
Figure 3:
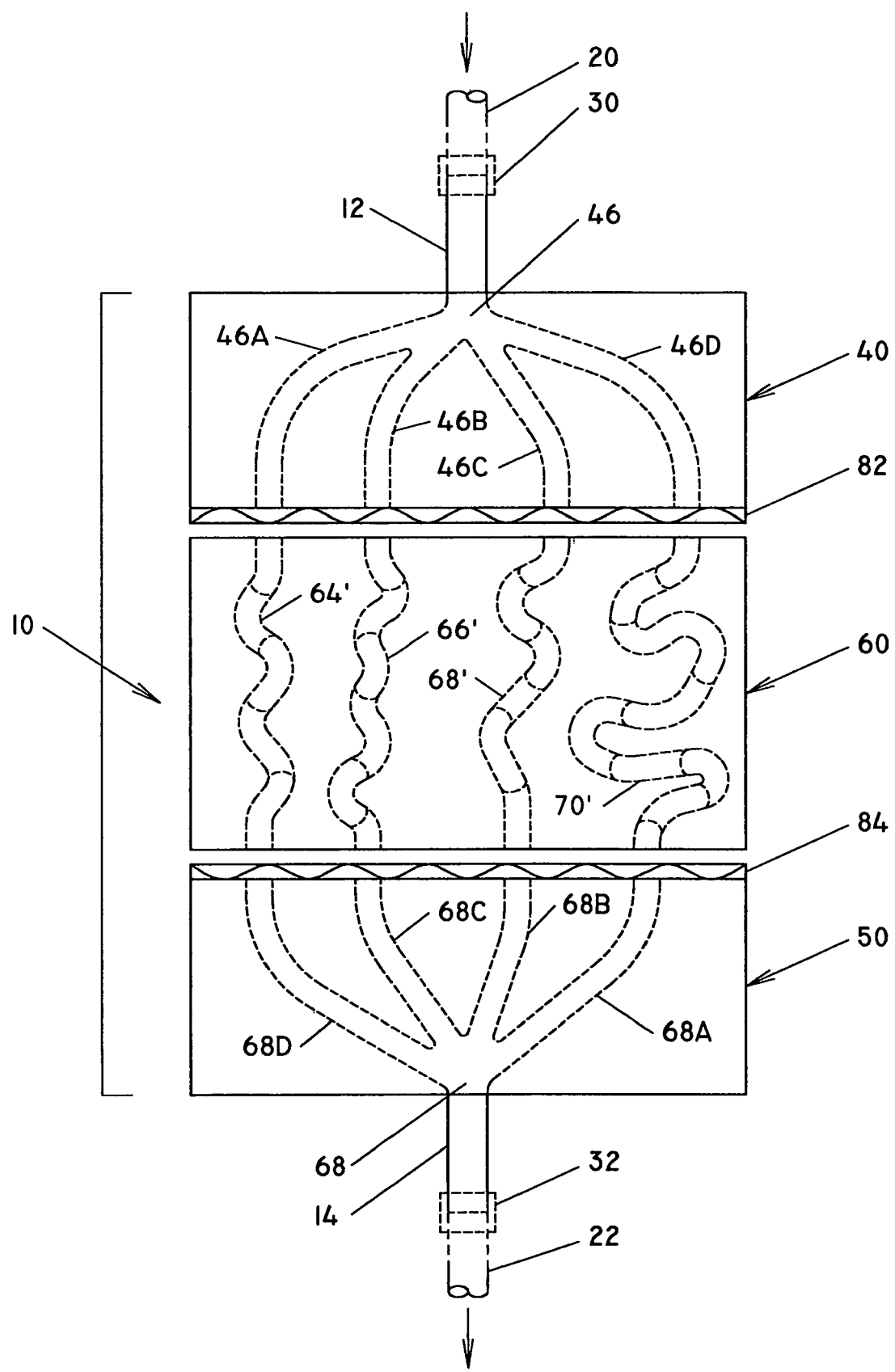
FIG. 3 is a cross-sectional view of another configuration of a micro-reactor of the present invention.

Referring again to FIG. 1, the top portion 40 of micro-reactor 10 is shown to include connection extension 12, and the bottom portion 50 is shown to include connection extension 14. The top and bottom portion of the micro-reactor are typically made of a durable material such as but not limited to, stainless steel, nickel alloy, titanium alloy, etc. The top and bottom portion of the micro-reactor are also typically made of the same material, but this is not required. As illustrated in FIGS. 2A and 2B, the top portion and bottom portion include a cavity 42, 52 respectively which is designed and sized to receive and encapsulate a middle portion 60 when the top and bottom portions are positioned together. As can be appreciated, the top and/or bottom portions can be designed without a cavity. As illustrated in FIG. 3, the top and bottom portions do not include a cavity, thus do not encapsulate the middle portion between the top and bottom portions. As can be appreciated, the top or bottom portion can be designed with a cavity that can substantially fully receive the middle portion and the other portion is merely designed to cover the bottom of the cavity to encapsulate the middle portion between the top and bottom portion. As can further be appreciated, many other configurations for the top and bottom portions can be used to partially or fully encapsulate the middle portion of the micro-reactor. Positioned at the base of each cavity is a securing flange 44, 54 respectively. As can be appreciated, the top and/or bottom portions of the micro-reactor can be designed without a flange. The securing flanges are used to help secure the top and bottom portions of the micro-reactor together. As can be appreciated, one or more clamps, bolting arrangements, locks, rivets, etc. can be used in conjunction with the flanges to secure the top and bottom portions of the micro-reactor together. The flanges can also and/or alternatively be connected together by welding, soldering or brazing metal. As shown in FIGS. 1, 2A and 2B, the flanges are connected together by a brazing metal 80 which will be discussed in more detail below.

As shown in FIGS. 1, 2A and 2B, the top and bottom portions are typically designed to encase the middle portion 60 to provide protection to the middle portion. As will be discussed below, the middle portion typically is at least partially formed of a catalyst material. This catalyst may be made of a precious material and/or may be made of material that is adversely affected by atmospheric conditions (e.g., water, oxygen, nitrogen, carbon dioxide, etc.). The encasing provided by the top and bottom portions provides protection to the middle portion. However, the middle portion can be exposed as illustrated in FIG. 3. As illustrated in FIGS. 2A, 2B and 3, the top and bottom portion can include one or more passageways to direct reactants into and/or receive reactants and/or products from the middle portion. As illustrated in FIGS. 2A and 2B, the top portion 40 includes a single passageway 46 and the upper surface. The bottom portion 50 also includes a single passageway 56. Passageway 46 directs reactants into a passageway 62 in the middle portion which divides into two passageways 64, 66 and then reforms at the base of the middle portion into a single passageway 68. The reactants and/or formed products are then directed into passageway 56 to direct the materials out of the micro-reactor. As illustrated in FIG. 3, the top and bottom portions can have a plurality of passageways. Connection extension 12 feeds reactants into the single passageway 46 in top portion 40. Passageway 46 then splits into four passageways 46a, 46b, 46c and 46d. The four passageways then direct the reactants into four passageway 64', 66', 68', 70' in middle portion 60. After the reactants and/or products have passed through the middle portion, they flow into passageways 68a, 68b, 68c, 68d in bottom portion 50 and then merge into single passageway 68 near the base of the bottom portion. As can be appreciated, many other passageway configurations can be utilized in the micro-reactor.

As illustrated in FIGS. 2A, 2B and 3, the passageways through the portions of the micro-reactor can take on many different shapes. Typically the passageways are tubular, but this is not required. In FIG. 3, the passageways have a generally uniform cross-sectional shape and size. The length and route through the middle portion of each of the passageways is shown to be different. In FIGS. 2A and 2B, the passageways do not maintain a uniform cross-section shape and size. The route through the middle portion of each of the passageways is shown to be different. As can be appreciated, one or more of the passageways can have the same shape, length and/or size. As can also be appreciated, the passageways can all have different shapes, lengths and/or sizes. The size, shape and/or length of one or more passageways in the top, bottom and/or middle portions of the micro-reactor can be selected to achieve certain flow rates, reactor resident times, pressure profiles, temperature profiles, catalyst exposure times, mixing profiles, etc.

Figure 4:
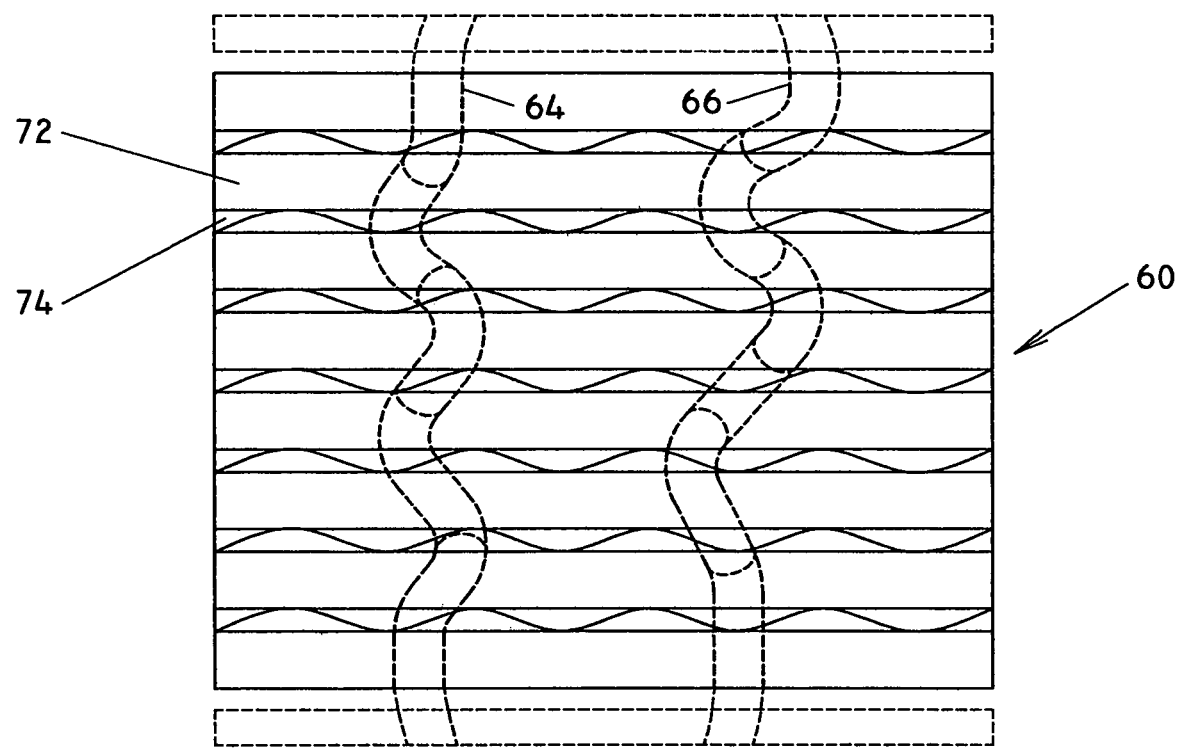
FIG. 4 is a cross-sectional view of a middle portion of the micro-reactor.
Figure 5:
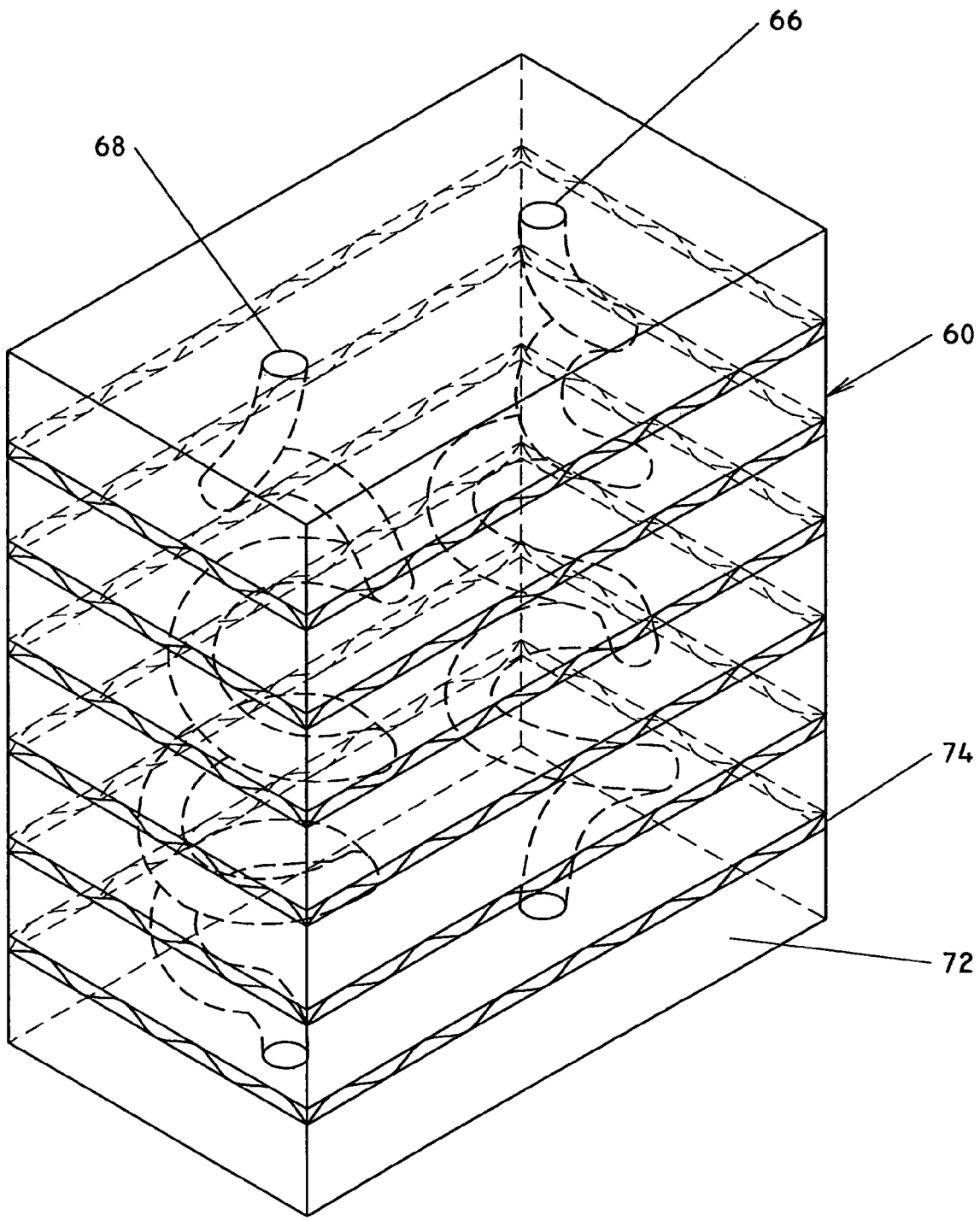
FIG. 5 is an elevation view of another arrangement of a middle portion of the micro-reactor.

Referring now to FIGS. 4 and 5, the construction of a portion of the micro-reactor is illustrated. The portion illustrated is the middle portion; however, the top and/or bottom portion of the micro-reactor can be formed in a similar manner. Alternatively, the top and/or bottom portion can be a molded, machined and/or cast component. As shown in FIGS. 4 and 5, the middle portion is formed of a plurality of metal foil layers 72 that are connected together by a brazing metal 74. The process for manufacturing the middle portion of the micro-reactor is illustrated in FIG. 6.

Figure 6:
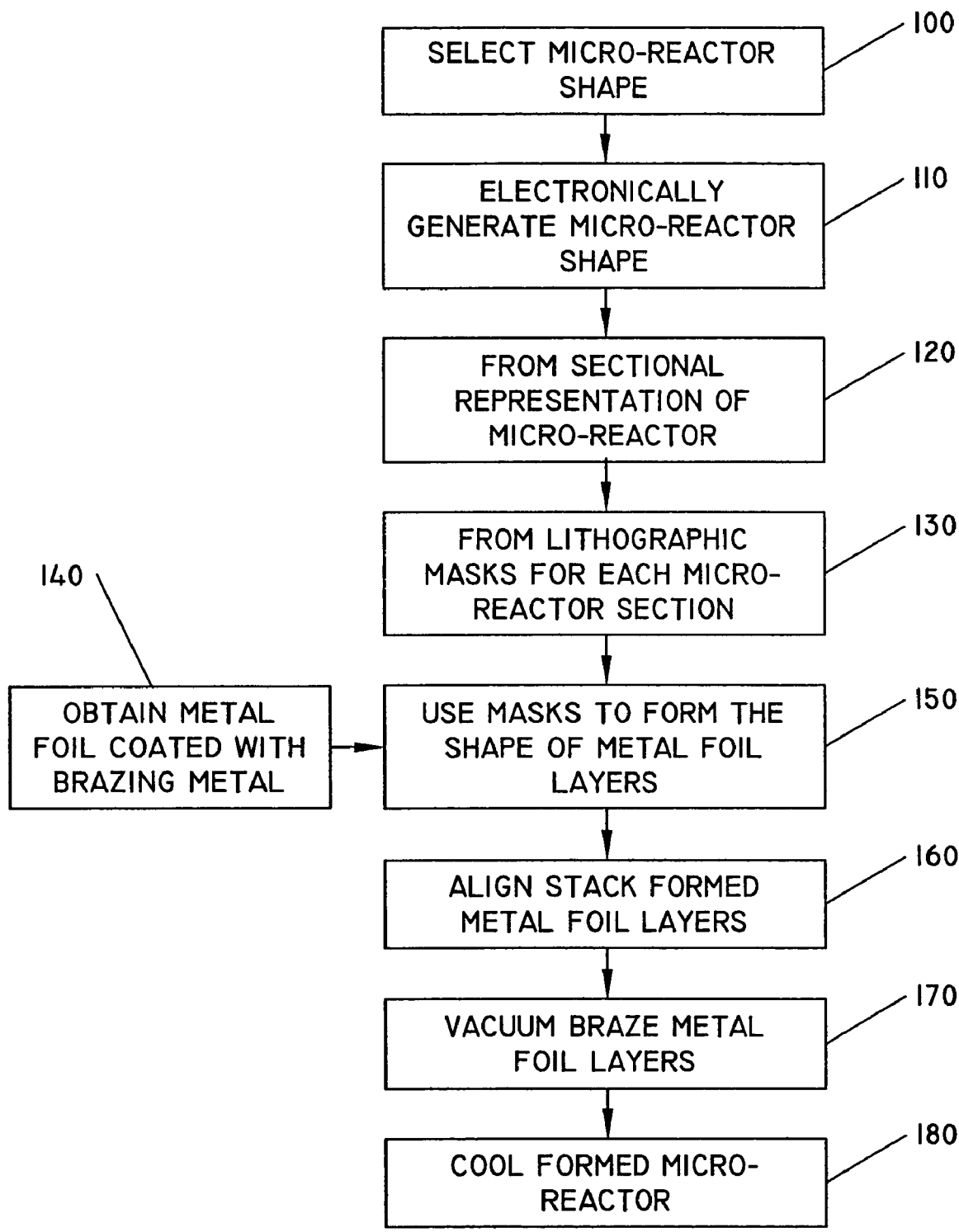
FIG. 6 is a flow chart illustrating a method of forming one or more portions of the micro-reactor.

As shown in FIG. 6, the first step of the manufacturing process 100 is to determine the desired shape of the micro-reactor. Typically the process engineer in charge of a particular chemical process will have or provide the particular specifications for the micro-reactor to be used in the particular chemical process. The drawing of the micro-reactor may be a mechanically drawn device and/or may be an electronically generated device.

Once the desired shape of the micro-reactor is determined, the shape of the micro-reactor is electronically entered 110 so as to form a three-dimensional computer generated image of the micro-reactor. As can be appreciated, each portion of the micro-reactor can be electronically entered, or only the portions of the micro-reactor that are to be formed by the process can be electronically entered. For purposes of the following description, the top, bottom and middle portion of the micro-reactor are to be formed by the process. One software package that can be used to generate the three-dimensional computer generated micro-reactor is AutoCAD. Many other CAD software programs or other types of drawing programs can be used.

After the micro-reactor is electronically entered, the drawing is electronically sectioned or sliced into a plurally of cross-sections 120. The sections or slices of the micro-reactor are taken along a single axis (e.g., longitudinal, vertical, horizontal, etc.). The thickness of each section or slice of the micro-reactor is representative of the thickness of the metal foil to be used to form the micro-reactor. The thickness of the metal foil is typically very thin, thus many sections or slices of the micro-reactor need to be electronically generated. Each of the sections also includes one or more holes or slots that will be used to orient the formed foil layers and also be used to maintain the position of the formed foil layers during heating and cooling of the foil layers. Typically these holes or slots are positioned about the periphery of the each section; however, the holes or slots can be positioned in other locations.

Once the sections or slices of the micro-reactor are generated, a lithographic mask is produced 130 for each foil layer to be used to form the micro-reactor. Each lithographic mask defines the features of each unique foil layer of the micro-reactor. The process for producing lithographic masks are well known in the art, thus will not be further described herein.

After the lithographic masks are produced for each foil layer of the micro-reactor, metal foil that is coated with a brazing metal is obtained 140. As can be appreciated, the coated metal foil can be obtained prior to the formation of the lithographic masks. The metal foil that is used to form the micro-reactor can be any type of metal. When forming the top and bottom portions of the micro-reactor, the metal foil is typically a durable metal such as stainless steel, nickel alloy, titanium alloy, etc. When forming the middle portion, a special metal may be used, such as a metal that catalyzes and/or facilitates in catalyzing a chemical reaction. Many types of these metals can be used such as, but not limited to, aluminum, cobalt, copper, gold, iridium, lithium, molybdenum, nickel, platinum, palladium, rhodium, ruthenium and/or silver, etc. As can be appreciated, the middle portion can be formed of the same type of metal foil layer or be formed of two or more different metal layers. For instance, half of the metal foil layers can be formed from gold and half of the metal foil layer can be formed from platinum. Many other combinations can be used to enable reactants to be exposed to one or more metals that catalyzes and/or facilitates in catalyzing a chemical reaction as the reactant pass through the micro-reactor. As can be appreciated, the top and/or bottom portion of the reactor can be made of the same or similar materials as the middle portion. As can further be appreciated, the top and/or bottom portion of the micro-reactor can be formed of a single metal foil layer or a plurality of different metal foil layers. The thickness of the metal foil used in the present invention is generally about 40–150 microns. As can be appreciated, other metal thickness can be used. The metal foil is also coated on one or both sides by a brazing metal. The coating of the brazing metal is typically by an electroplating process; however, other coating processes can be used. The coating thickness of the brazing metal is typically about 0.2–1.5 microns; however, other thicknesses can be used. The brazing metal can be any type of brazing material that can be used to successfully secure two adjacent positioned metal foil layers together and provide the desired connection strength. The brazing material for all the metal foil layers can be the same or can be different. When different materials are used for the metal foil layers, typically at least two or more of the metal foil layers are connected together with different types of brazing metals; however, this is not required.

Once the coated metal foil is obtained, the metal foil is subjected to lithographic micro-machining techniques and/or micro-machining techniques 150 to produce patterned metal foil layers that are ultimately used to form the micro-reactor. Some of the micro-machining techniques that can be used include photo-etching and reactive ion etching.

After the foil layers have been formed, the foil layers are aligned and stacked 160 to form the desired three-dimensional shape. The foil layers should be stacked so that a brazing metal exists between each foil layer. This arrangement can be achieved in a number of different ways. One non-limiting way is to have one side of each of the foil layers coated with the brazing metal. The alignment of the foil layers can also be accomplished in a variety of ways. Typically alignment pins or other fixed structures are used to align the multiple layers of metal foil. The holes or slots in the metal foil are inserted onto the alignment pins thereby properly orienting the foil layers with respect to one another.

The aligned and stacked metal foil layers are then subjected to heat 170 so as to braze together the metal foil layers. The heating of the coated metal foil layer at a proper elevated temperature for a sufficient time will result in the metal coating to melt and flow between the metal layers. Typically, the brazing process is conducted under a vacuum; however, this is not required. The heating of the metal foil layers typically occurs in an inert atmosphere; however, this is not required. During the heating process, the metal foil layers expand. The alignment holes or slots maintain the foil layers in alignment during this heating process. Typically the alignment holes or slots in each foil layer are sized and shaped to account for the expansion of the foil layers during heating. As such, when the foil layers are heated at or near their maximum temperature, wherein the brazing material is partially or fully liquified, the holes or slots line up relative to the alignment pins so as to form the desired shaped of the micro-reactor.

Once the metal foil layers are heated for a sufficient time, the formed micro-reactor is cooled 180. When the foil layers are cooled, the brazing material solidifies thereby locking the foil layers in position relative to one another. The alignment holes or slots in the foil layers are sized and shaped so as to allow the locked together foil layers to contract during cooling. Typically, the cooling occurs in an inert atmosphere; however, this is not required. The use of the above method to manufacture a micro-reactor results in a cost effective process to manufacture a micro-reactor that has a specific design for use in a particular chemical process. FIGS. 4 and 5 illustrate a section of a middle portion of a micro-reactor that has been formed by the above-described process. Middle portion 60 includes a plurality of metal foil layers 72 that are connected together by brazing metal 74.

The following example illustrates the manufacture of the middle portion of a micro-reactor that is formed of platinum in accordance with the present invention. The manufacturing process of the present invention can provide methods for fabricating portions of a micro-reactor having three-dimensional passageway configurations that are difficult, if not impossible to make by conventional manufacturing processes.

The first part of the manufacturing process involves the generation of a three-dimensional computer model of the middle portion of the micro-reactor. The computer generated model of the middle portion is divided into a plurality of thin sections that are cut parallel to the longitudinal axis of the middle portion. The thickness of the sections is substantially uniform and reflects the thickness of the metal foil to be used to make the middle portion. Guide holes or slots are also inserted for each section. The number, size and shape of the guide holes or slots are selected to achieve the proper orientation of the foil layers during the heating and cooling of the foil layers.

The metal foil used to form the middle portion is platinum having a thickness of about 30–150 microns. The metal foil is coated on one side with a thin metal electroplated layer of a brazing metal having a thickness of about 0.1–10 microns. Non-limiting examples of brazing metals for the metal coating include nickel-silver alloys. A specific example of a coated metal foil for use in manufacturing the middle portion of the micro-reactor is a platinum metal foil coated on one side with a electroplated nickel-silver alloy layer wherein the thickness of the platinum foil is about 77 microns, the thickness of the nickel-silver alloy coating is about 1 micron and the total thickness of the coated metal foil is about 78 microns. In this example, the sliced sections of the computer generated middle portion of the micro-reactor would represent sections having a thickness of about 78 microns. The middle portion would thus be formed from about 100–3000 layers of metal foil.

Each of the coated metal foil sheets of are chemically etched to match a specific section of a computer generated section of the middle portion. Photo-masks were produced for etching each of the metal foil layers. Each metal foil layer was processed using standard photo-etching techniques and were etched in such a way that the cross-sectional shape of the etched walls for each layer are perpendicular to the top and bottom surfaces of the layer (commonly referred to as straight sidewalls).

Once all the metal foil layers were etched, the metal foil layers were stacked together in order to form the middle portion. The guide holes or slots were used to orient the foil layers on graphite guide pins. The metal foil was specifically coated such that a nickel layer existed between each metal foil layer. The stacked metal foil layers were then bonded together by a vacuum brazing process. During the brazing process, the layered assembly was heated in a inert atmosphere (e.g. argon, nitrogen, hydrogen, etc.) to a temperature of 100–1300° C. for about 20–75 minutes, which caused the coated nickel-silver alloy layer to flow thereby wetting the surfaces of the tungsten foil layers. The temperature and time of heating was sufficient to allow the nickel to uniformly flow and connect the layers of platinum foil together at all contact points. The brazed layers of platinum foil were then cooled in an inert atmosphere for about 1–3 hours and then removed. The formed middle portion was removed from the guide pins and then inspected for quality control purposes to determine if the formed middle portion was properly formed in accordance with the desired specifications.

Figure 7:
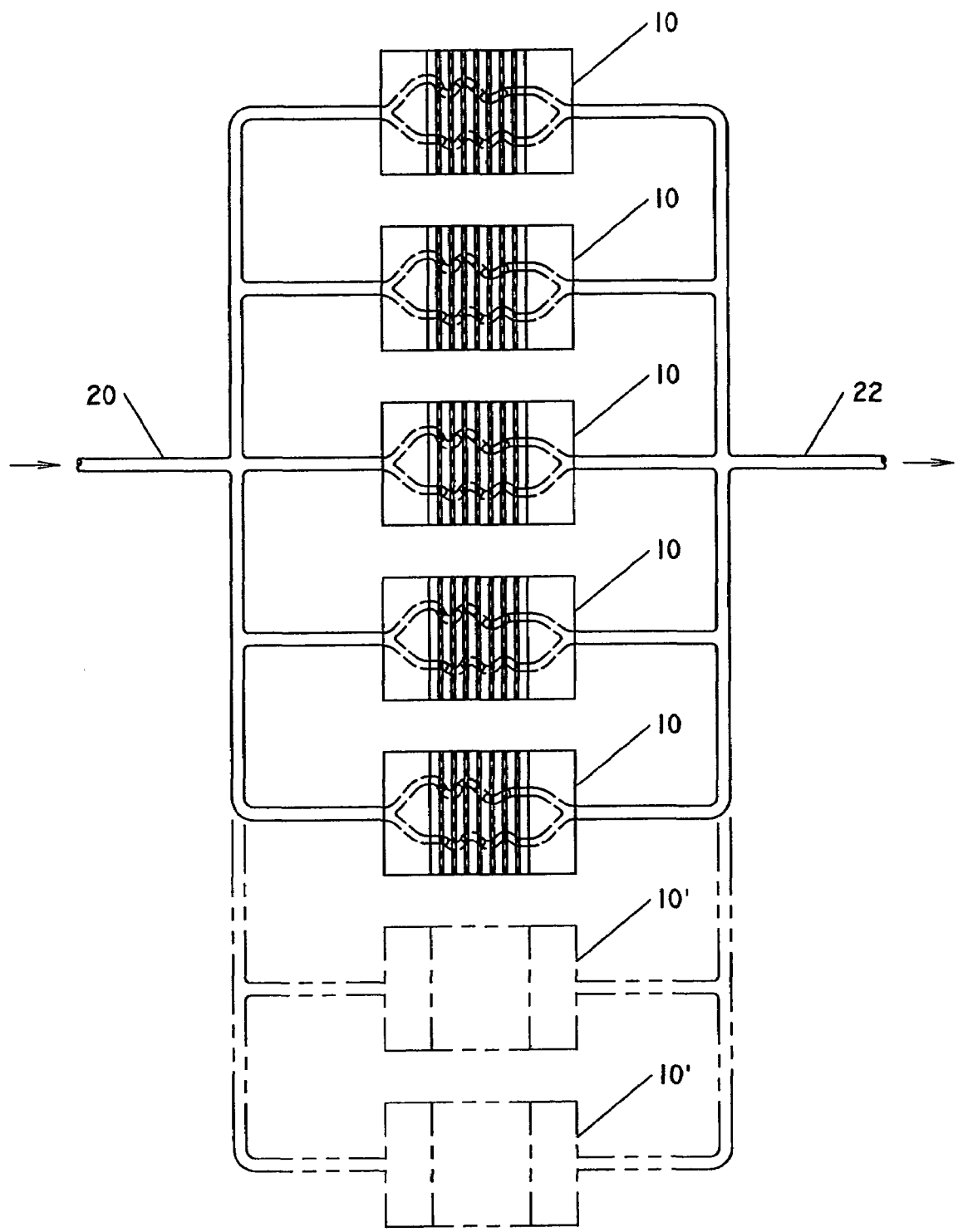
FIG. 7 is a graphical illustration of a plurality of micro-reactors positioned in series in a chemical process; and, FIG. 8 is a flow chart illustrating a method of recovering metal catalyst from the middle portion of the micro-reactor.

Referring now to FIG. 7, There is illustrated a plurality of micro-reactors 10 connected between pipes 20 and 22. FIG. 7 illustrates that the number of micro-reactors used in a process can be easily increased or decreased depending on present production rates. In addition, one or more of the micro-reactors can be taken out of service without having to shut down the chemical process. For example, a line to one of the micro-reactors may become clogged or the catalyst in one micro-reactor may be fouled or spent. To correct this problem, the pipeline feeding the particular micro-reactor is shut off and the micro-reactor is replaced or pipes feeding the micro-reactor are serviced. If one of the micro-reactors is taken out of service, one or more of micro-reactors 10' can be placed in service so that little or no interruption of the chemical process occurs. In prior reactor system wherein a single large reactor was used, the chemical process was typically terminated so that the reactor could be serviced (e.g. cleaned, replace catalyst, etc.). The use of the micro-reactors of the present invention enable a chemical process to typically not be shut down due to the need to service a particular micro-reactor.

Figure 8:
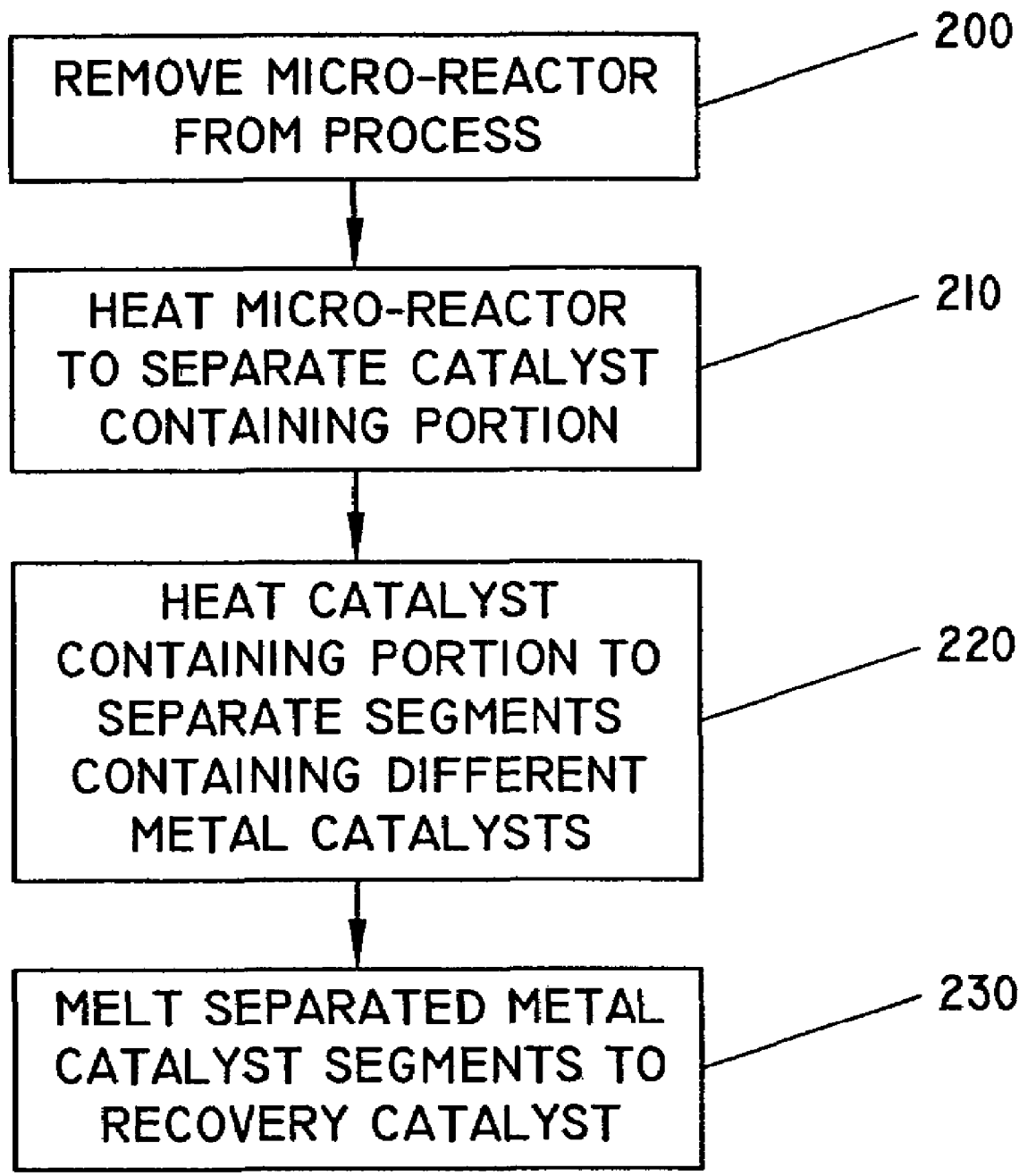

Referring now to FIG. 8, there is illustrated a flow chart for a process of recovering a catalyst in one or more portions of the micro-reactor. When the micro-reactor is formed of a top portion, a bottom portion and one or more middle portions, the one or more middle portions typically include a catalyst. In many types of chemical reactions, the catalyst is a precious metal that is highly desirable to recover. Consequently, once the catalyst is spent or fouled in the reactor, the reactor is sent to a recovery facility to recover the precious metal of the catalyst. Typically the whole reactor is melted down and the precious metal is then separated by expensive and time consuming techniques. Other techniques include exposing the reactor to high energy plasma to melt the reactor and/or catalyst support to thereby recover the catalyst. This process is also time consuming and expensive. The micro-reactor of the present invention overcomes the past difficulties and high costs associated with catalyst recovery. The first step is to remove the micro-reactor from a chemical process line as shown in step 200. Once the micro-reactor is removed from the process line, the micro-reactor is disassembled. As illustrated in FIGS. 1, 2A and 2B, the top and bottom portions of the micro-reactor are secured together at flanges 44, 54 by a brazing metal 80. In practice, the melting point of brazing metal 80 is less than the melting point of the brazing metal that secures together the foil layer of the middle portion, and the top portion and bottom portions if one or both of these portion are form from foil layers. By selecting a brazing metal having this lower melting temperature, the micro-reactor can be heated to or slightly above the melting point of brazing metal 80 to enable the top and bottom portions to be separated from one another without causing any of the foil layers of the middle portion, top portion or bottom portion to separate. This is step 210 as shown in FIG. 8. If the top and bottom portions of the micro-reactor are mechanically connected together, this heating step can be ignored.

As shown in FIG. 3, the middle portion of the micro-reactor is connected to the top portion by brazing metal 82 and to the bottom portion by brazing metal 84. The middle portion is typically connected to the top and/or bottom portion by a brazing metal, but this is not required. For instance, the middle portion can be encapsulated between the top and bottom portion as shown in FIGS. 1, 2A and 2B without having to be connected to the top and/or bottom portions. When the middle portion is connected to the top and/or bottom portion as illustrated ion FIG. 3, the melting point of brazing metal 82 and 84 is less than the melting point of the brazing metal that secures together the foil layer of the middle portion, and the top portion and bottom portions, the lower melting temperature of the brazing metal layers 82 and 84 allows the micro-reactor to be heated to or slightly above the melting point of brazing metal 82 and 84 to enable the top and bottom portions to be separated from one another without causing any of the foil layers of the middle portion, top portion or bottom portion to be separated. This step is again illustrated as step 210 shown in FIG. 8.

Once the middle portion of the micro-reactor is separated from the top and bottom portions of the micro-reactor, the metal in the one or more separated portions can be simply recovered by melting the individual portions as represented in step 230.

When the middle portion of one or more of the other portions of the micro-reactor are formed from metal foil layers of different metals, the different metal foil layers are separated prior to the melting and recovery step 230. This separation step is illustrated as step 220 of FIG. 8. For example, if the middle portion is formed of two catalyst metals such as gold and platinum, the gold and platinum layers are separated from one another prior to melting the foil layers. This separation can be accomplished by selecting a brazing metal that melts at a certain temperature. If, for example, the middle portion was formed of 1000 foil layers and layers 1–400 were formed of gold and layers 410–1000 were made of platinum, the brazing metal between layers 400 and 401 would be selected to have a lower melting point that the brazing metal used to connected together layers 1–400 and layers 401–1000. As such, the middle portion could be heated to the melting point or slightly above the melting point of the brazing metal between layers 400 and 401 so as to soften or melt this brazing metal without causing the brazing metal between layers 1–400 and 401–1000 to melt. Consequently, layer 1–400 and 401–1000 can be simply separated from one another and then melted in separated facilities in accordance with step 230. As can be appreciated, the brazing metals selected to connect one or more portions of the micro-reactor together, and/or one or more foil layers of a portion together can used to control the separation of various sections of the micro-reactor in an orderly manner to form and disassemble the micro-reactor as desired.

Although the method of the present invention has been particularly directed to the manufacture of micro-reactors, the technology of the present invention can be used in other fields of use. Among the many conceivable fields of use, technology areas, and devices which can utilize the method of manufacture of the present invention include, but are not limited to, the automotive industry in the fields of inertial measurement, micro-scale power generation, pressure measurement, fluid dynamics and the like (e.g., accelerometers, rate sensors, vibration sensors, pressure sensors, fuel cells, fuel processors, nozzle technology, valves and regulators, pumps, filters, catalytic converters, relays, actuators, heaters, etc.), the avionics industry in the fields of inertial measurement, RF technology, communications, active structures and surfaces and the like (e.g., conformable MEMS (active and passive), micro-satellite components, microthrusters, RF switches, antennas, phase shifters, displays, optical switches, accelerometers, rate sensors, vibration sensors, pressure sensors, fuel cells, fuel processors, nozzle technology, valves and regulators, pumps, filters, relays, actuators, heaters, etc.), the biological, biotechnology and chemical industry in the fields of micro-fluidics, microbiology, DNA assays, chemical testing, chemical processing other than the use of micro-reactors, lab-on-a-chip, tissue engineering, analytical instrumentation, bio-filtration, test and measurement, bio-computing, biomedical imaging and the like (e.g., biosensors, bioelectronic components, reaction wells, microtiterplates, pin arrays, valves, pumps, microwells and microwell arrays, microvalves, micropumps, valve seats, valve actuators (diaphragm), cavity chamber, actuator diaphragm, bio-filters, SEM, EDS, ICP, x-ray mapping, x-ray crystallography, tissue scaffolding, screens, filters, microscopes, cell sorting and filtration membranes, etc.), the medical (diagnostic and therapeutic) industry in the fields of imaging, computed tomography, angiography, fluoroscopy, radiography, interventional radiography, orthopedic, cardiac and vascular devices, catheter based tools and devices, non-invasive surgical devices, medical tubing, fasteners, surgical cutting tools and the like (e.g., airways, balloon catheters, clips, compression bars, stents, drainage tubes, ear plugs, microwells and microwell arrays, microvalves, micropumps, drug delivery chips, microwell detectors, gas proportional counters, valve seats, valve actuators (diaphragm), cavity chamber, actuator diaphragm, hearing aids, electrosurgical hand pieces and tubing, feeding devices, balloon cuffs, wire/fluid coextrusions, lumen assemblies, infusion sleeves/test chambers, introducer tips/flexible sheaths, seals/stoppers/valves, septums, shunts, implants, prosthetic devices, membranes, electrode arrays, ultra-sound transducers, infra-red radiation sensors, radiopaque targets or markers, scatter grids, detector arrays, etc.), the military industry in the fields of weapon safeing, arming and fusing, miniature analytical instruments, biomedical sensors, inertial measurement, distributed sensing and control, information technology and the like (e.g., MEMS fuse/safe-arm devices, ordinance guidance and control devices, gyroscopes, accelerometers, GPS, disposable sensors, spectrometers, active MEMS surfaces (large area), micro-mirror MEMS displays, etc.), the telecommunications industry in the fields of optical switches, displays, adaptive optics, and the like (e.g., micro-relays, optical attenuators, photonic switches, micro-channel plates, optical switches, displays, etc.), and the extrusion industry in the field die plates, dies and the like. As can be appreciated, many other devices can be made by the manufacturing process of the present invention.

While considerable emphasis has been placed herein on preferred embodiments of the invention, it will be appreciated that other embodiments can be devised and that many changes can be made in the preferred embodiments without departing from the principles of the invention. Accordingly, it is to be distinctly understood that the foregoing descriptive matter is to be interpreted merely as illustrative of the invention and not as a limitation.

I claim:

1. A method of manufacturing at least portion of a micro-reactor comprising:
    providing a plurality of metal foil layers;
    forming a plurality of metal foil layers into specific shapes by use of at least one lithographic technique;
    stacking and aligning said plurality of formed metal layers;
    connecting together said plurality of formed metal layers to form said portion of said micro-reactor; including the step of generating a computer image of said portion of said micro-reactor and then sectioning said computer image of said portion of said micro-reactor into a plurality of sectional images that correspond to a plurality of said formed metal foil layers.

2. The method as defined in claim 1, wherein a plurality of said metal foil layers are formed of a catalyst metal.

3. The method as defined in claim 1, wherein a plurality of said metal foil layers each have an average thickness less than about 400 microns.

4. The method as defined in claim 1, wherein said at least one lithographic technique includes photo-etching.

5. The method as defined in claim 1, wherein said step of forming includes the formation of at least one alignment opening in at least one metal foil layer.

6. The method as defined in claim 5, wherein said step of stacking and aligning includes the use of at least one alignment opening formed in a plurality of metal foil layers.

7. The method as defined in claim 1, wherein said step of connecting together includes brazing together a plurality of metal foil layers.

8. The method as defined in claim 7, including the step of coating at least one side of a plurality of metal foil layers with a brazing metal.

9. The method as defined in claim 7, wherein said brazing metal has an average coating thickness of less than about 10 microns.

10. The method as defined in claim 7, wherein said step of brazing includes vacuum brazing.

11. The method as defined in claim 1, including the step of generating a computer image of a plurality of said formed metal foil layers.

12. The method as defined in claim 1, including the step of forming at least one mask from at least one of said computer images and at least partially forming at least one of said formed metal foil layers using said mask.

13. The method as defined in claim 1, including the step of forming at least one mask from at least one of said sectional images and at least partially forming at least one of said formed metal foil layers using said mask.

14. A method of manufacturing at least portion of a micro-reactor comprising:
    selecting a micro-reactor shape having at least one passageway in said micro-reactor, said at least one passageway adapted to allow flow of at least one reactant through at least a portion of said micro-reactor;
    generating a computer image of a plurality of metal foil layers, a plurality of said metal foil layers including an opening that at least partially forms at least one passageway in said micro-reactor;
    forming a plurality of metal foil layers into specific shapes by use of at least one lithographic technique based at least partially on said generated computer image;

stacking and aligning said plurality of formed metal layers, said metal foil layers being stacked and aligned to at least partially orient at least one opening in a plurality of said metal foil layers to at least partially form said at least one passageway in said micro-reactor; and, connecting together said plurality of formed metal layers to form at least a portion of said micro-reactor.

15. The method as defined in claim 14, wherein a plurality of said metal foil layers has a thickness of less than about 400 microns.

16. The method as defined in claim 14, wherein said opening in said metal foil layer has a maximum cross-sectional width of about 5000 microns.

17. The method as defined in claim 15, wherein said opening in said metal foil layers has a maximum cross-sectional width of about 5000 microns.

18. The method as defined in claim 14, wherein said at least one passageway in said micro-reactor includes a catalyst.

19. The method as defined in claim 17, wherein said at least one passageway in said micro-reactor includes a catalyst.

20. The method as defined in claim 18, wherein at least a portion of a wall of said passageway is formed of said catalyst.

21. The method as defined in claim 19, wherein at least a portion of a wall of said passageway is formed of said catalyst.

22. The method as defined in claim 20, wherein at least one of said metal foil layers includes a catalyst metal, said catalyst metal at least partially promoting a reaction of said at least one reactant.

23. The method as defined in claim 14, wherein a plurality of metal foil layers are connected together by a brazing metal, said brazing metal having a different composition from said metal foil layer.

24. The method as defined in claim 21, wherein a plurality of metal foil layers are connected together by a brazing metal, said brazing metal having a different composition from said metal foil layer.

25. The method as defined in claim 23, wherein said brazing metal has an average coating thickness of less than about 10 microns.

26. The method as defined in claim 23, wherein said step of brazing includes vacuum brazing.

27. The method as defined in claim 14, wherein said step of aligning said plurality of metal foil layers includes aligning at least one alignment opening in said metal foil layer with another alignment opening in another metal foil layer.

28. The method as defined in claim 24, wherein said step of aligning said plurality of metal foil layers includes aligning at least one alignment opening in said metal foil layer with another alignment opening in another metal foil layer.

29. The method as defined in claim 14, wherein a plurality of metal foil layers includes at least two openings to form a plurality of passageways in said micro-reactor.

30. The method as defined in claim 28, wherein a plurality of metal foil layers includes at least two openings to form a plurality of passageways in said micro-reactor.

* * * * *